(12) United States Patent
Matsuura et al.

(10) Patent No.: US 9,095,650 B2
(45) Date of Patent: Aug. 4, 2015

(54) PRECISION FLUID DELIVERY SYSTEMS

(75) Inventors: David G. Matsuura, Encinitas, CA (US); Philip J. Simpson, Escondido, CA (US); Helen Anderson, Encinitas, CA (US)

(73) Assignee: FLEX PARTNERS, INC., Encinitas, CA (US)

( * ) Notice: Subject to any disclaimer, the term of this patent is extended or adjusted under 35 U.S.C. 154(b) by 441 days.

(21) Appl. No.: 13/499,251

(22) PCT Filed: Oct. 6, 2010

(86) PCT No.: PCT/US2010/051707
§ 371 (c)(1),
(2), (4) Date: May 9, 2012

(87) PCT Pub. No.: WO2011/044294
PCT Pub. Date: Apr. 14, 2011

(65) Prior Publication Data
US 2012/0215200 A1    Aug. 23, 2012

Related U.S. Application Data

(60) Provisional application No. 61/249,145, filed on Oct. 6, 2009.

(51) Int. Cl.
*A61M 5/00* (2006.01)
*A61M 5/142* (2006.01)
(Continued)

(52) U.S. Cl.
CPC ......... *A61M 5/14216* (2013.01); *A61M 5/1422* (2013.01); *A61M 5/3129* (2013.01); *A61M 5/31511* (2013.01); *A61M 5/16809* (2013.01); *A61M 2005/31598* (2013.01)

(58) Field of Classification Search
CPC ............... A61M 5/14216; A61M 5/16809; A61M 5/31511; A61M 5/31525; A61M 5/31576
USPC ........................ 604/207, 211, 215, 223, 231
See application file for complete search history.

(56) References Cited

U.S. PATENT DOCUMENTS

| | | |
|---|---|---|
| 1,689,419 A | 10/1928 | Bronander |
| 3,168,872 A | 2/1965 | Pinkerton |

(Continued)

FOREIGN PATENT DOCUMENTS

| | | |
|---|---|---|
| WO | WO 96/26754 | 9/1996 |
| WO | WO 00/44420 | 8/2000 |

(Continued)

OTHER PUBLICATIONS

Fluid Metering, Inc., Dispensers & Metering Pumps, www.fmipun-np.com (2 pages) downloaded Oct. 19, 2011.

(Continued)

*Primary Examiner* — Kevin C Sirmons
*Assistant Examiner* — Deanna K Hall
(74) *Attorney, Agent, or Firm* — Knobbe Martens Olson & Bear, LLP

(57) ABSTRACT

A precision syringe (10) can comprise an annular fluid pathway (16) and annular plunger (12) sealing received within the annular fluid pathway. Various precision pumps (50, 200, 300, 400, 500, 600, 700, 800, 900, 1000, 1100, 1200, 1300, 1400, 1500, 1600, 1700) are configured for discrete displacement of precise volumes of fluid. The precision pumps can operate by reciprocating movement to expand and contract a cavity (204, 304, 404, 504, 604, 704, 804, 904, 1040, 1104, 1204, 1304, 1404, 1504, 1604, 1704). Fluid can be introduced by movement along an axis or rotation about an axis of one or members forming, in whole or in part, the cavity. Associated methods are also disclosed.

12 Claims, 38 Drawing Sheets

(51) Int. Cl.
*A61M 5/31* (2006.01)
*A61M 5/315* (2006.01)
*A61M 5/168* (2006.01)

(56) References Cited

U.S. PATENT DOCUMENTS

| | | | |
|---|---|---|---|
| 3,464,359 A | 9/1969 | King et al. |
| 4,008,003 A | 2/1977 | Pinkerton |
| 4,037,616 A | 7/1977 | Pinkerton |
| 4,054,522 A | 10/1977 | Pinkerton |
| 4,099,548 A | 7/1978 | Sturm et al. |
| 4,178,240 A | 12/1979 | Pinkerton |
| 4,197,196 A | 4/1980 | Pinkerton |
| 4,405,294 A | 9/1983 | Albarda |
| 4,941,809 A | 7/1990 | Pinkerton |
| 5,058,779 A | 10/1991 | Surdilla |
| 5,127,449 A | 7/1992 | Mueller et al. |
| 6,004,117 A | 12/1999 | Brunk |
| 6,475,188 B1 | 11/2002 | Baxter |
| 6,840,404 B1 | 1/2005 | Schultz et al. |
| 7,207,780 B2 | 4/2007 | Bach |
| 7,963,937 B2 | 6/2011 | Pauser et al. |
| 8,187,228 B2 * | 5/2012 | Bikovsky | 604/152 |
| 8,202,250 B2 † | 6/2012 | Stutz |
| 8,287,495 B2 † | 10/2012 | Michaud |
| 8,298,184 B2 † | 10/2012 | Diperna |
| 8,414,535 B2 † | 4/2013 | Jacobsen |
| 2004/0241023 A1 | 12/2004 | Pinkerton, III |
| 2005/0276705 A1 | 12/2005 | Pinkerton, III |
| 2010/0065579 A1 * | 3/2010 | DiPerna | 222/1 |
| 2011/0144586 A1 † | 6/2011 | Michaud |
| 2011/0152824 A1 † | 6/2011 | DiPerna et al. |

FOREIGN PATENT DOCUMENTS

WO 2005039674 A1 † 5/2005
WO 2007074363 A2 † 7/2007

OTHER PUBLICATIONS

International Search Report and Written Opinion of the International Searching Authority for International Application No. PCT/US2010/051707 mailed on Nov. 30, 2010.

\* cited by examiner
† cited by third party

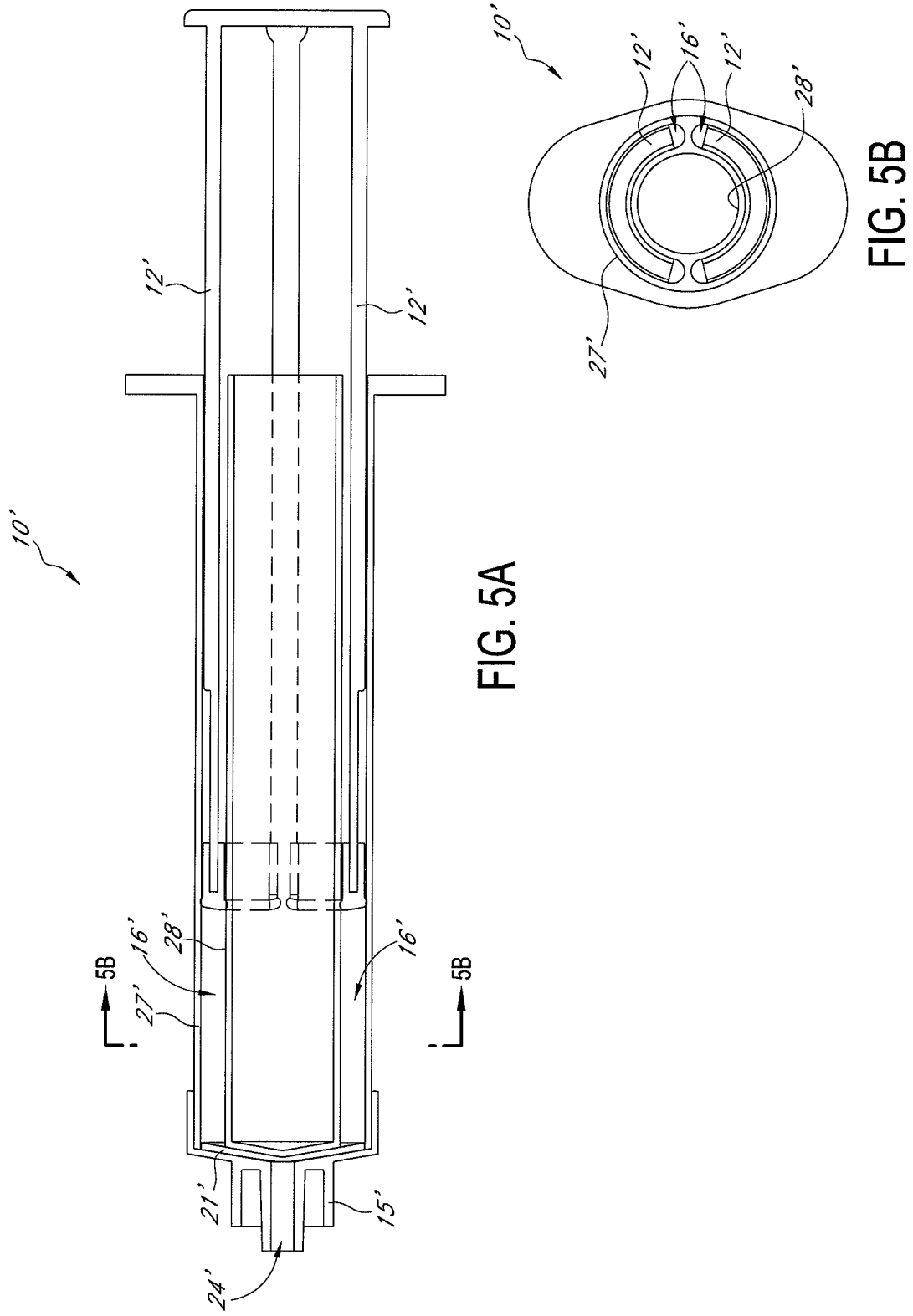

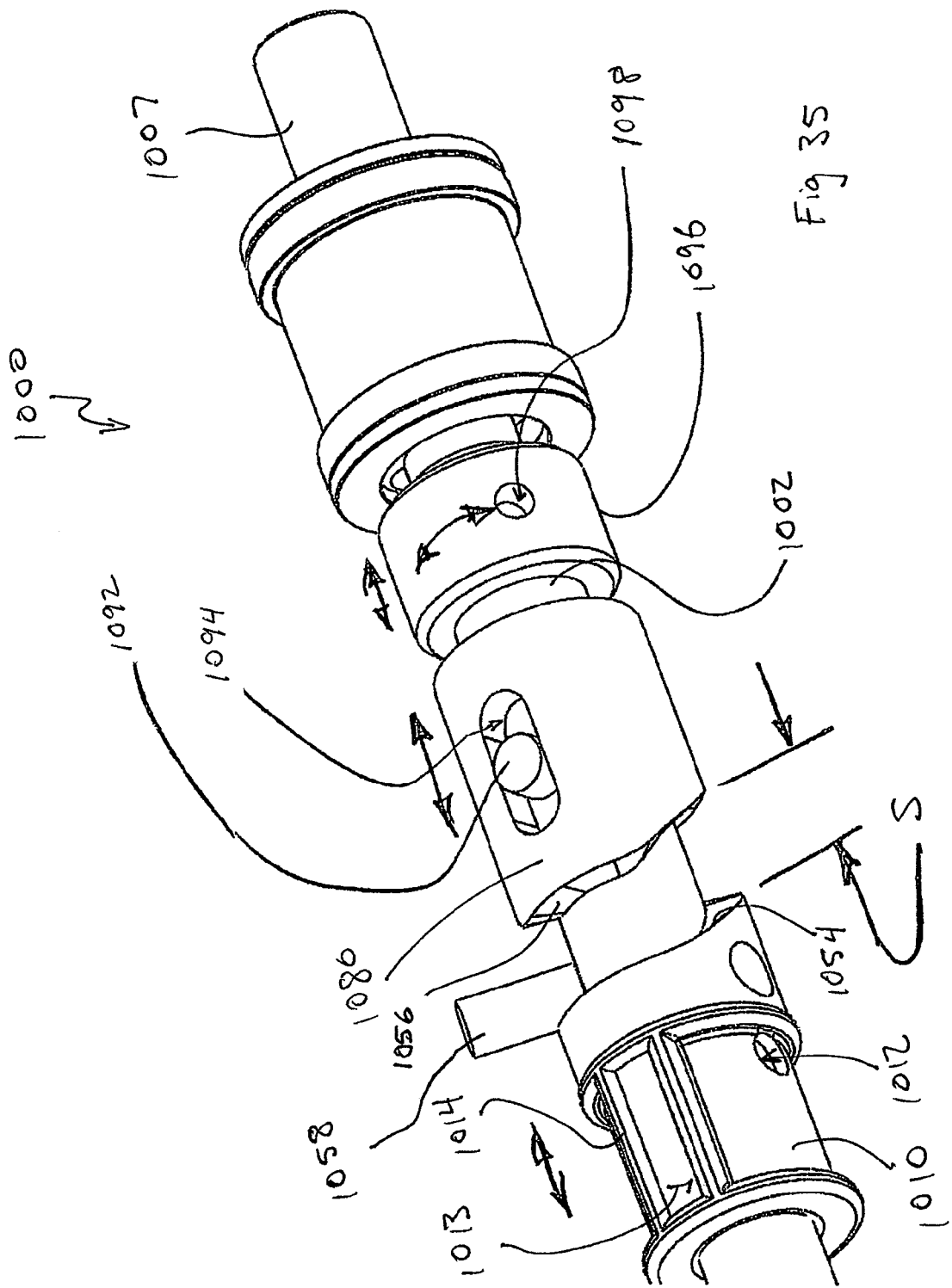

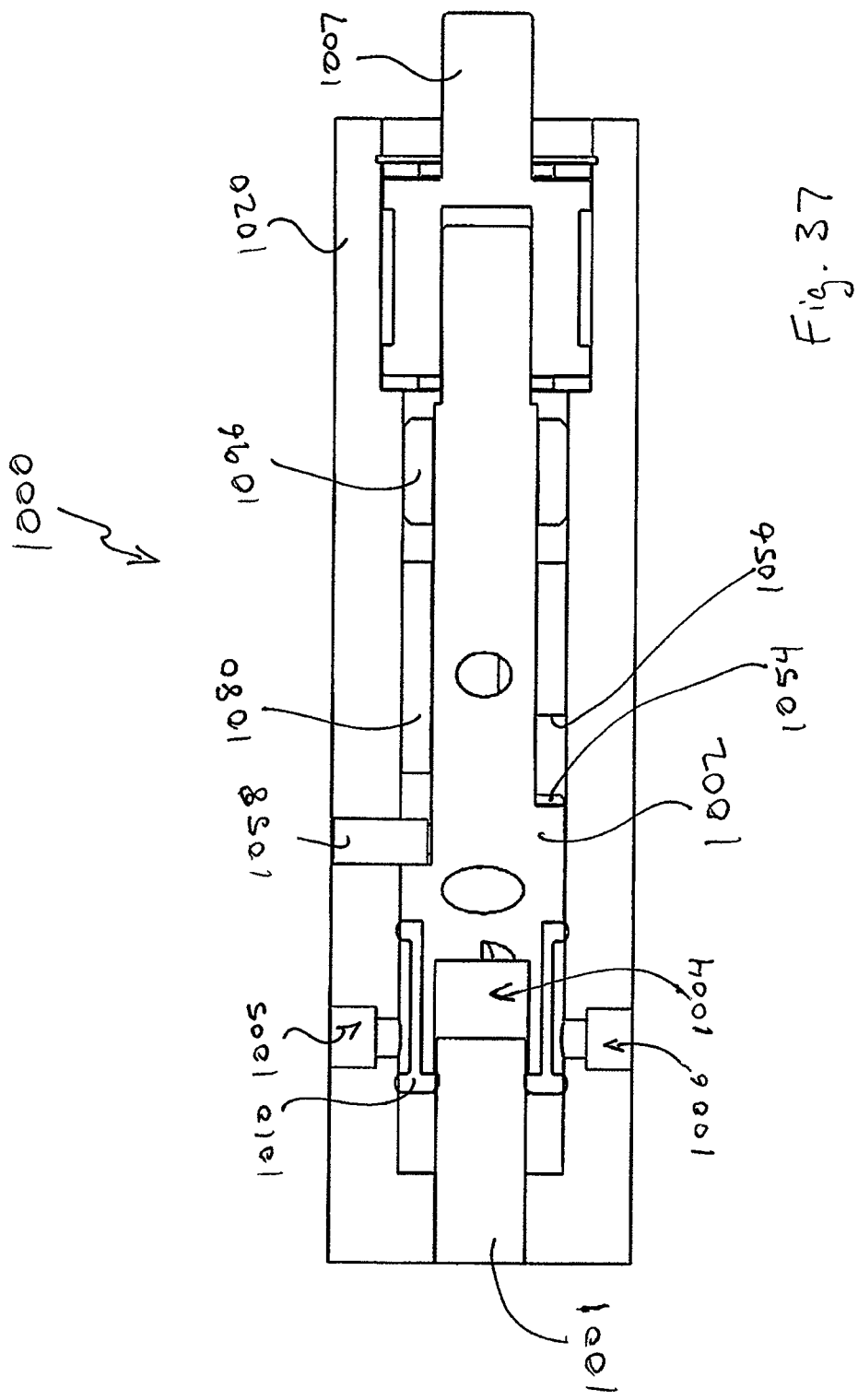

US 9,095,650 B2

PRECISION FLUID DELIVERY SYSTEMS

CROSS-REFERENCE TO RELATED APPLICATIONS

This application is the U.S. National Phase application under 35 U.S.C. §371 of International Application PCT/US2010/051707 filed on Oct. 6, 2010 which claims the benefit of U.S. Provisional Patent Application No. 61/249,145, filed on Oct. 6, 2009 and entitled "Precision Fluid Delivery Systems," which are both hereby expressly incorporated by reference herein in its entirety.

FIELD OF THE DISCLOSURE

The present disclosure relates generally to the delivery of small and precise volumes from a precision syringe and precision pump.

BACKGROUND OF THE DISCLOSURE

Syringes are commonly used for the delivery of fluids in the medical field and are oftentimes adapted to syringe pumps in order to attempt to deliver fluids at a constant volumetric rate. Typically, as smaller dispensing volumes with greater precision are desired, syringes with smaller diameter barrels are used in order to decrease the cross-sectional area of the fluid being forced out of the syringe by the plunger. The smaller the cross-sectional area of fluid within the syringe barrel, the smaller the volume of fluid that will be dispensed when the plunger is advanced a given distance. Therefore, to achieve the delivery of increasingly smaller volumes of fluid (e.g. fractions of a microliter), it is necessary for the syringe plunger to advance in increasingly shorter distances.

It is typically the case with pulse modulated syringe pumps that the plunger is unable to advance in small enough increments so that a series of small boluses (e.g. fractions of a micro liter) average out to a desired low flow rate. In such cases where a pulse modulated syringe pump is unable to advance in small enough increments, the remedy is oftentimes delivering larger volumes (boluses) of fluid less frequently so that over a period of time the desired flow rate is achieved. Negative outcomes can result from delivering some medications to patients in significantly larger boluses than the recommended drug delivery rate. Additionally, it is increasingly difficult to move a syringe plunger at increasingly shorter distances due to the difficulties associated with the plunger having to overcome sticktion (static friction). It is well known to those skilled in the art that the fluid sealing portion of the plunger has to overcome the friction of the seal by initially requiring a greater force than what is necessary to advance the plunger once the plunger has begun to advance. Therefore, it becomes increasingly difficult to control increasingly shorter advancements of a plunger and achieve high dispensing volume precision.

SUMMARY OF THE DISCLOSURE

As noted above, for given distance of plunger advancement in a syringe, the volume of fluid that will be dispensed is reduced as the cross-sectional area of fluid within the syringe barrel is reduced. However, diminution of the cross-sectional area of fluid within the syringe barrel is limited by, for example, manufacturing capabilities. Also, if the cross-sectional area of fluid within the syringe barrel of a syringe is too small, that syringe may not a fit into currently available syringe pumps, have insufficient fluid capacity, or both.

A common type of syringe pump uses a leadscrew mechanism to advance the syringe plunger and dispense fluid from the syringe adapted to the syringe pump. For these commonly used syringe pumps to have improved precision at lower dispensing volumes, a high pitch thread on the leadscrew would be optimal. However, the high pitch thread is not beneficial for the dispensing of larger volumes and thus would require added costs for medical facilities which would have to purchase additional syringe pumps to accommodate different dispensing requirements.

It is desirable to have a standard size and shape syringe, or one that can be easily adapted to a number of standard syringe pumps (e.g. pulse modulated, leadscrew) for the delivery of small and precise volumes. This would remedy a present drawback of the currently used standard sized syringes which are unable to deliver small enough boluses at a high enough precision. Moreover, this would alleviate situations where larger than recommended boluses are being delivered in order to achieve a lower average fluid flow rate which can cause the person being administered the drug to experience unnecessary suffering and physiological strain. Therefore, there is a need for a fluidic delivery system that can provide the benefits of adapting to currently available syringe pump systems while being able to deliver very small volumes with high precision, which is particularly beneficial for applications in the medical field (e.g. drug delivery, pediatrics). Additionally, it is desirable to implement the concepts associated with dispensing small volumes with high precision into pumping mechanisms.

Various embodiments disclosed herein are directed at addressing at least one of the needs and eliminating, or at least reducing, the effects of the shortcomings of the prior art, such as those described above for example.

At least some of the embodiments disclosed herein serve to remedy the need for a delivery device that can deliver small (e.g. fractions of micro-liters) and precise volumes from a standard size and shape syringe so that those embodiments can be easily adapted to current syringe pump systems being used (e.g. in medical facilities). Some embodiments include a precision syringe device that has a barrel and an inner column that travels generally the entire length of the barrel and a plunger that is configured to travel generally the length of the barrel. The inner column extends generally along the center axis of the barrel. The syringe barrel and inner column are generally cylindrical in shape, but can be any number of other shapes and sizes. The plunger provides a fluidic seal between the inner column and barrel at its distal end and functions to force the contents within the barrel of the syringe out of the dispensing end of the syringe as the plunger is advanced toward the dispensing end of the syringe. The plunger is shaped such that it provides a fluidic seal between the outer wall of the inner column (shown in this example to have a generally circular cross section) and the inside wall of the barrel (shown in this example to have a generally circular cross section).

A typical syringe has a barrel and a plunger with the distal end of the plunger (where the plunger contacts the fluid within the barrel) sized and shaped to have generally the same cross section as the inner diameter of the barrel of the syringe. This allows the distal end of the plunger to provide a fluidic seal around the inner diameter of the barrel, thereby having the ability to force contents within the syringe out of the barrel through the nozzle of the syringe as the plunger is advanced through the barrel. The fluid flow rate is calculated by determining the area of the cross section of fluid that is being pushed by the plunger through the barrel and multiplying the calculated cross section by the rate at which the plunger is being longitudinally advanced along its centerline. Therefore, for the typical syringe, the cross-sectional area of the fluid for determining the fluid flow rate is calculated to be the cross-sectional area of the inside diameter of the syringe barrel. Once the cross-sectional area is calculated (SA1), it can be multiplied by the rate at which the plunger is advanced (distance per unit of time) to determine the fluid flow rate of the contents being dispensed from the syringe. In addition, the volume dispensed can simply be determined using the calculated cross-sectional area (SA1) and multiplying it by the distance that the plunger is advanced toward the dispensing end of the syringe.

Various embodiments disclosed herein utilize the same concept of calculating fluid flow rate and volume dispensed by calculating the cross-sectional area of the fluid within the barrel of the syringe and multiplying it by the rate or distance at which the plunger is advanced. Therefore, the cross-sectional area of the fluid in the precision syringe barrel is determined by subtracting the calculated cross-sectional area of the inner column from the calculated cross-sectional area within the inner diameter of the barrel. This cross-sectional area (SA2) can then be used to determine the fluid flow rate and volume dispensed, as described above.

Some embodiments disclosed here provide the benefit of having similar size and shaped outer body profiles of a standard syringe, but has a smaller fluid cross-sectional area (SA2) than the fluid cross-sectional area of the standard syringe (SA1). Again, this is due in part to the inner column that is contained and takes up volumetric space within the barrel and results in an annular flow of the fluid through the syringe. The shape and diameter of the inner column and barrel can be of any number of characteristics and dimensions in order to produce the most desirable dispensing precision and flow rate over a given distance that the plunger is advanced.

By way of example, a standard syringe barrel may have the same inside and outside diameters as the inside and outside diameters of the syringe barrel of an exemplifying embodiment, but the fluid cross-sectional area of the standard syringe will be greater than the fluid cross-sectional area of this exemplifying embodiment. Therefore, if a plunger were to advance the same distance in each of the aforementioned syringes, the volume dispensed would be significantly smaller with the precision syringes disclosed herein. As mentioned above, this is due in part to the inner column which reduces the cross-sectional area of the fluid within the syringe barrel resulting in a small annular flow of the fluid through (and dispensed out of) the syringe. This feature has several advantages of which will be discussed below and can be implemented in various configurations and dispensing mechanisms, such as a pump.

One advantage of some embodiments of the precision syringe disclosed herein is that the precision syringe can dispense significantly smaller dispensing volumes than currently available syringes, thus allowing the precision syringe to dispense small volumes with substantially greater precision. Additionally, some embodiments can adapt to syringe pumps currently being used (e.g. in medical facilities) that are designed to deliver larger, less precise volumes with standard syringes. By way of example, the use of some precision syringe embodiments can enable medical facilities to use their current syringe pumps to deliver smaller and more precise volumes of fluid while operating the current syringe pumps with appropriate conversion of the fluid delivery rate compared to the advancement rate of the pump's driver. In some embodiments, the pump can be modified to correlate or calculate the driver displacement rate with fluid delivery rate differently when a precision syringe is used than when a standard syringe is used. Some embodiments disclosed herein remedy the issues associated with using syringe pumps currently in use for the delivery of small volumes with greater precision.

Several embodiments of precision pumps are disclosed herein. One of the precision pump embodiments employs a similar concept as that described in the precision syringe by transferring small volumes of fluid via annular flow. In this first embodiment of the precision pump, the pistons which assist in transporting the fluid from the inlet port to the outlet port are shaped and dimensioned such that they take up a significant amount of volumetric space within the fluid pathway. This allows only a small amount of annular volumetric space provided for the transport of fluids. Therefore, smaller and more precise volumes of fluid are delivered by using the precision pump by way of annular flow. As is the case with the precision syringe, the stroke (linear travel of the pistons) necessary to deliver considerably small volumes of fluid are achievable with standard driving mechanisms (e.g. cams, linear actuators, rotary actuators). This allows certain embodiments of the precision pumps to be incorporated into a vast number of mechanical systems.

Additionally, precision pump embodiments are disclosed herein which form a cavity within a piston for transferring fluid from an inlet port to an outlet port. The cavity defines a specific volume that the precision pump fills and subsequently dispenses. One benefit of transferring fluids via a cavity formed within the piston is that the axial stroke required to fill and dispense fluids into and out of the cavity can be significantly reduced while still maintaining the ability to dispense small volumes with high precision. Therefore, the precision pumps which use a cavity to transport fluids from an inlet port to an outlet port can be implemented in devices and systems where there is limited space available or a compact design is desired (e.g. wearable devices, PCA's (patient-controlled analgesia)).

All of the precision pumps disclosed herein can be run open-looped since they transfer fluid by way of volume displacement. Therefore, the precision pumps disclosed herein can, in some embodiments, maintain a consistent dispensing volume per cycle over generally the lifetime of the precision pump. This makes the need for additional hardware (e.g. flow control, pressure control) and software optional for monitoring the pump output. Furthermore, any of the concepts disclosed herein can be adapted to any number of driving mechanisms (e.g. cams, motors) and systems.

It has also been contemplated that any of the dispensing devices and systems disclosed herein (e.g. precision syringe, precision pumps) can be used for at least one of transferring more than one type of fluid, mixing at least two different types of fluid, and dispensing fluid out of more than one dispensing port (e.g. precision pump with multiple outlet ports). One benefit associated with having the ability to mix at least two different types of fluid within a compact fluid dispensing device or system, such as the example embodiment disclosed herein, is that there is a need, for example, for compact drug delivery devices which can mix different reagents or medications immediately prior to the injection of a drug cocktail into a person. It is becoming increasingly common for drug delivery to be administered by the patient via hand-held (e.g. insulin delivery pen) and user-wearable devices (e.g. for controlled and continuous insulin delivery). The ability for fluid dispensing systems and fluid mixing and subsequent dispensing systems to achieve a more compact configuration and have the ability to mix drug cocktails immediately prior to injection has limited the currently available user-wearable devices, which are known to improve the quality of life of patients due to having a more manageable and consistent delivery of necessary medications without requiring the patient to make doctor visits or transport cumbersome drug delivery devices. The precision fluid delivery devices disclosed herein have the ability to scale to a size that is small enough to result in a wearable drug delivery device while also enabling the mixing of a drug cocktail immediately prior to injection.

As disclosed above, one benefit of the fluid delivery devices disclosed herein is that they are all scalable (both large and small) to meet the needs of their intended use. Another precision pump embodiment disclosed herein demonstrates an example of integrating a precision pump such that the precision pump can be used to overcome deficiencies in the prior art. For example, a precision pump embodiment can be appropriately scaled and adapted to at least one fluid reservoir. The precision pump and adapted fluid reservoir(s) can then be assembled as the disposable sub-assembly to a non-disposable sub-assembly. What makes the fluid delivery devices disclosed herein a good option as disposable devices is that they require a small number of inexpensive parts. Furthermore, the reservoir allows a large amount of fluid to be directly transferred through the precision pump, which can be easily removed when emptied (along with the precision pump) and replaced with a new reservoir and precision pump. Therefore, the fluid delivery devices disclosed herein are optimal as at least part of a disposable and/or single use component.

All of the concepts and embodiments disclosed herein can be manually or programmably operated and are adjustable to dispense any size of volumes necessary. Furthermore, it should be emphasized that the fluid delivery devices disclosed herein can be used and/or implemented into any number of systems for the delivery of fluids (e.g. biologics, fuel, adhesives, industrial compounds) or other substances (e.g. gels, adipose), and not solely for the delivery of medication. Additionally, the fluid delivery devices have been contemplated to adapt to patches for the delivery of fluids and/or chemicals into a person, and not solely to the commonly used injection needle. By way of example only, the fluid delivery device can deliver very small (e.g. fractions of a microliter) doses of fluid into at least a portion of a patch attached to a person's arm which would allow the person's skin to absorb the fluid within the patch at a generally determined rate.

BRIEF DESCRIPTION OF THE DRAWINGS

FIG. 5A is a cross-sectional view, similar to that of FIG. 2, of a precision syringe comprising two chambers and two plungers, according to an embodiment.

FIG. 5B is a cross-sectional view of the precision syringe of FIG. 5A.

FIG. 35 is an isometric view of a portion of a precision pump comprising a floating cam and a cam-motion limiter that can be adjusted to vary the volume of fluid transferred within a cavity, according to an embodiment.

FIG. 37 is a full cross-sectional view of the precision pump of FIGS. 35 and 36.

DETAILED DESCRIPTION OF EXEMPLIFYING EMBODIMENTS

Figure 1:
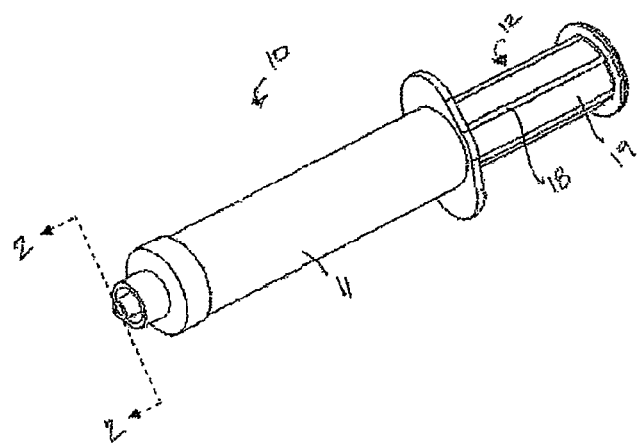
FIG. 1 is a perspective view of a precision syringe according to an embodiment.

Several embodiments are described below by way of illustration and example. To maintain clarity of the present disclosure, not all features of an actual implementation are described in this specification. In other words, the present disclosure is directed to enabling one of ordinary skill in the art to practice the novel and inventive features disclosed herein. Aspects which are known to those of ordinary skill in the art or which can be ascertained without undue experimentation have been omitted in some instances. It is respected that if one is to pursue the development of any embodiment, either disclosed or similar to one disclosed, decisions will be required as to how to apply the claimed invention to best accommodate specific goals (e.g. compliance with systems, desired output). Moreover, it will be appreciated that such a development effort might be complex and time-consuming, but would nevertheless be a routine undertaking for those of ordinary skill in the art having the benefit of this disclosure. A variety of inventive features and components that warrant patent protection, both individually and in combination, are disclosed in connection with the precision syringes and precision pumps described below and shown in the accompanying figures.

Exemplifying Embodiments of Precision Syringes

FIGS. 1-5 illustrate a precision syringe 10 according to an exemplifying embodiment. The precision syringe 10 includes a barrel 11 with an interior chamber 16 and a plunger 12, which are illustrated to have a generally cylindrical profile and be generally concentrically aligned when mated. The barrel 11 includes a plunger insertion end 13 and a dispensing end 14 with the plunger insertion end 13 providing an opening 25 to the interior chamber 16 for the plunger 12 to be inserted and removed from within the barrel 11. The plunger 12 is dimensioned to slidably travel longitudinally along the shared central axis 26 (if present) of the barrel 11 and provide at least a fluidic seal at its distal end 17 along the walls of the interior chamber 16. A nozzle 15 is located at the dispensing end 14 of the barrel 11 where the contents contained within the interior chamber 16 can be dispensed upon advancement of the plunger 12 in the direction of the dispensing end 14.

Figure 2:
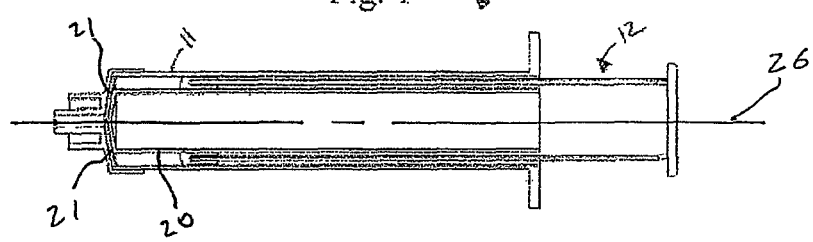
FIG. 2 is a cross-sectional view of the precision syringe of FIG. 1 taken along line 2-2 of FIG. 1.

FIG. 2 shows a cross section of the precision syringe 10 from FIG. 1 which illustrates the inner column 20 and dispensing channels 21 located within the barrel 11. In the illustrated embodiment, the inner column 20 travels generally the entire length of the interior chamber 16 generally along the center axis of the barrel 11. The barrel 11 can comprise an outer wall 27 and an inner wall 28. The interior chamber 16 can be provided within the outer wall 27 and the inner column 20 can be defined by the inner wall 28. One function of the inner column 20 can be to take up volumetric space within the interior chamber 16. Preferably, the inner column 20 does not contain a fluidic pathway, but can contain a fluidic pathway (e.g. for the dispensing of a second fluid) in some embodiments.

Figure 3:
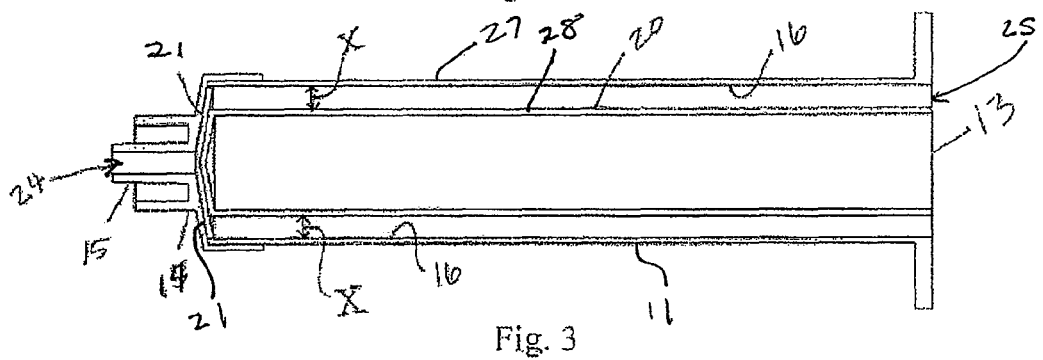
FIG. 3 is a cross-sectional view of the syringe barrel of the precision syringe of FIG. 1.

With reference to FIGS. 2 and 3, the dispensing channels 21 allow the contents contained within the interior chamber 16 to be dispensed out the nozzle 15 through the dispensing through hole 24. The dispensing channels 21 provide a fluidic pathway from the interior chamber 16 to the dispensing through hole 24. Although the dispensing channels 21 are shown as narrow channels, they can have other configurations in other embodiments.

The inner column 20 is dimensioned to have a cross section such that the distance between the outer diameter of the inner column 20 (or the inner wall 28) is a specific distance X (shown in FIG. 3) from the inner diameter of the outer wall 27 (the outer diameter of the interior chamber 16). The dimension X is preferably small so that the cross-sectional area of the space provided for fluidic contents within the interior chamber 16 is relatively small. This arrangement can allow a high precision of small volumes to be dispensed from the precision syringe 10 without requiring the advancement of the plunger to be infinitesimally or unfeasibly small. The distance X may be any dimensional value depending on the requirements (e.g. dispensing volumes, flow rate, dispensing volume precision) of the precision syringe 10.

Figure 4:
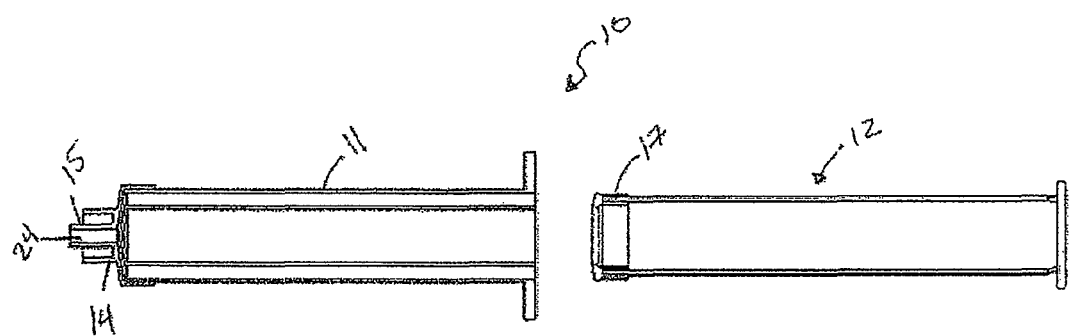
FIG. 4 is an exploded view of the precision syringe of FIG. 1.
Figure 5:
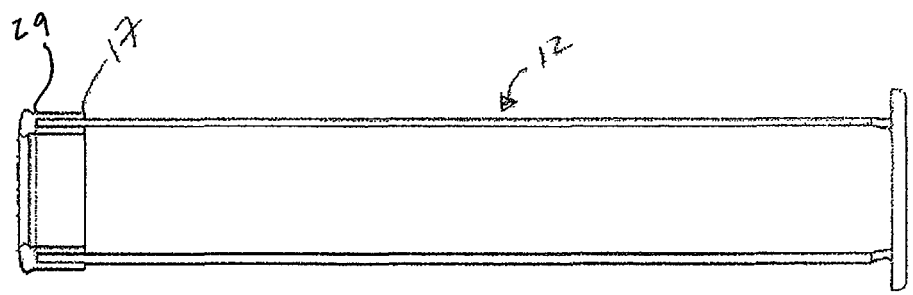
FIG. 5 is a cross-sectional view of the syringe plunger of the precision syringe of FIG. 1.

The plunger 12, shown for example in FIGS. 4 and 5, is configured to travel generally the length of the interior chamber 16 which, in the illustrated embodiment, extends from approximately the dispensing channels 21 to the plunger insertion end 13 of the barrel 11. The interior chamber 16 and inner column 20 are generally cylindrical in shape, but can have other shapes in some embodiments. Similarly, while the illustrated interior chamber 16 and inner column 20 have a generally circular cross-sectional shape, they can have other cross-sectional shapes in some embodiments. Thus, the outer wall 27 and the inner wall 28 of the barrel 11 can have cylindrical configurations with a cross-sectional shape that is circular or other shape.

The plunger 12 provides a fluidic seal at its distal end 17 against the walls of the interior chamber 16 between the inner column 20 (or the inner wall 28) and the outer wall 27. The plunger 12 is shown in the illustrated embodiment to be annular in shape such that it provides a fluidic seal between the outer wall of the inner column 20 (which preferably has a generally circular cross section) and the outer wall of the interior chamber 16 (which also preferably has a generally circular cross section). In the illustrated embodiment, a compressible material (e.g. rubber) encapsulates the distal end 17 of the plunger and assists in providing the fluidic seal. The encapsulating portion 29 can provide a fluidic seal against both the outer wall 27 and the inner wall 28 in some embodiments, as illustrated in FIGS. 2 and 5. In some embodiments, the precision syringe can comprise one or more separate sealing members to independently seal or substantially seal against each of the outer wall 27 and the inner wall 28.

In the embodiment illustrated in FIG. 1, runners 18 travel along all or a majority of the plunger stem 19 and protrude radially out from the plunger stem 19. In other embodiments, the runners can protrude radially inward form the plunger stem 19. The runners 18 generally come into contact with the inside walls of the interior chamber 16 when the plunger 12 is positioned within the barrel 11 and function to at least maintain a generally concentric alignment between the barrel 11 and plunger 12.

One benefit of the illustrated precision syringe is that it can be adapted to be used with syringe pumps that are currently being used since the outer profile of the precision syringe 10 can be shaped and dimensioned similar to the outer profile of the standard syringe. The inner column can simply be shaped and dimensioned to take up the necessary volumetric space within the interior chamber 16 so that the desired volume and flow rate is dispensed with the advancement of the plunger over a given distance or at a given rate.

In some embodiments, the inner column can provide the sole or a secondary fluid pathway, which would still have a small cross-sectional area, and the outer barrel would still have a standard syringe size and shaped outer profile. In embodiments in which the inner column provides the sole fluid pathway, the space surrounding the fluid pathway would take up volumetric space in the syringe, thus maintaining a small cross-sectional area to facilitate dispensing small volumes with high precision. Additionally, as illustrated in FIGS. 5A and 5B, a single syringe barrel 11' can be configured to include multiple interior chambers 16' and associated plungers 12' for the dispensing of more than one fluid from a syringe 10' with a standard size and shaped outer profile. In such embodiments, the fluids can mix in the nozzle 15' after passing through the dispensing channels 21', as illustrated in FIGS. 5A and 5B for example, or the fluids can mix within a chamber, separate from the nozzle, within the syringe before dispensing into the nozzle then out from the syringe. This would allow the fluids to mix immediately prior to being dispensed from the syringe. In some embodiments, the fluids can mix when, or immediately before, passing through the hole 24' of the nozzle 15'. In some embodiments, the fluids can be dispensed through separate nozzles, which can be arranged to be adjacent to each other or spaced apart from each other.

In the embodiment of FIGS. 5A and 5B, an annular space is divided along its length into two chambers 16'. In some embodiments, a precision syringe can comprise an annular space divided into two or more chambers along its length, multiple annular chambers concentrically arranged, or any combination of those. As described above, the fluid pathways and associated plungers of the multiple fluid dispensing syringe could be sized, shaped and configured (e.g. annular flow) to meet the needs of the desired dispensing volumes, ratio of dispensing volumes from each of the fluid pathways, and dispensing volume precision.

First Exemplifying Embodiment of a Precision Pump

FIGS. 6-11 illustrate a first exemplifying embodiment of a precision pump 50 which includes a first piston 51 and a second piston 52. First and second pistons 51, 52 are concentrically aligned with each other and are able to axially translate along their shared central axis independently and in concert with each other. The linear translation of the pistons 51, 52 are controlled by some type of mechanical driving mechanism which is shown in this example to be a cam system 60, but may be any number of driving mechanisms that cause the pistons 51, 52 to axially translate without departing from the scope of this invention. Additionally, more than two pistons and their associated driving mechanisms may be implemented into the system to transfer fluid between at least one inlet port 56 and at least one outlet port 54 in some embodiments.

Each piston 51, 52 has at least one o-ring 53 that provides a fluidic seal, with each o-ring specifically placed to facilitate the transfer of fluid from the inlet port 56 to the outlet port 54 of the precision pump 50. Although o-rings are shown in this exemplifying embodiment, any number of fluidic seals may be used in place of o-rings in some embodiments.

The pistons 51, 52 are shaped and dimensioned so that they can axially translate both independently from, and in concert with, each other to fill and dispense a specified volume of fluid between the mating feature 61 of the first piston 51 and the mating feature 62 of the second piston 52. In the illustrated embodiment, the mating feature 61 of the first piston 51 is shown as being a step from the outer diameter of the piston shaft down to a smaller outer diameter of the piston shaft (best shown in FIG. 8). The mating feature 62 of the second piston 52, in the illustrated embodiment, is generally a thin walled tube-like feature (shown in FIG. 8). The mating features 61, 62 are shaped and dimensioned so that when the mating features 61 and 62 separate, a volumetric space or cavity is formed between the mating features 61 and 62 of which fluid can then fill. Additionally, the mating feature 61, 62 are shaped and dimensioned so that when at least one of the pistons 51, 52 axially translates and forces the mating features 61, 62 in contact (or in closer proximity to each other), the fluid contained between the mating features 61, 62 is forced out through the outlet port 54. Although the mating features 61, 62 are shown in this example to be generally a stepped feature and a tube-like feature, the mating features 61, 62 can have other configurations that allow a space to be formed therebetween and transfer fluid from an inlet port 56 to an outlet port 54 in some embodiments. In some embodiments, the volumetric space or cavity can have an annular configuration, for example.

The implementation of pistons 51, 52 with large cross sections relative to the inside diameter of the fluidic pathway 55 between the inlet port 56 and the outlet port 54 can be advantageous in some embodiments, such as the one illustrated in FIGS. 6-11. This allows the pistons 51, 52 take up a majority of the volumetric space within the fluidic pathway 55 for small volumes (fractions of micro-liters) of fluid to flow along the annulus through the precision pump and dispense with high precision, as discussed above for example. In FIGS. 6-11, the fluidic pathway 55 is shown as a linear through hole which can be shaped and dimensioned in any number of suitable shapes and dimensions in various embodiments. The fluidic pathway 55 provides a pathway for the pistons 51, 52 to travel so that small volumes of fluid can annularly flow between the mating features of the pistons from the inlet port 56 to the outlet port 54.

Figure 6:
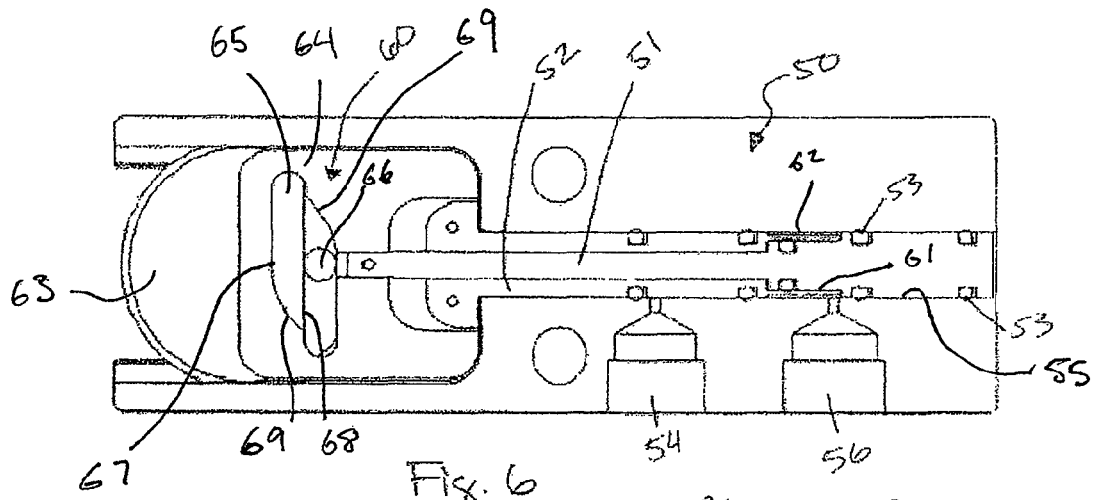
FIG. 6 is a cross-sectional view of a precision pump with an annular cavity according to an embodiment in a first position (P1).
Figure 7:
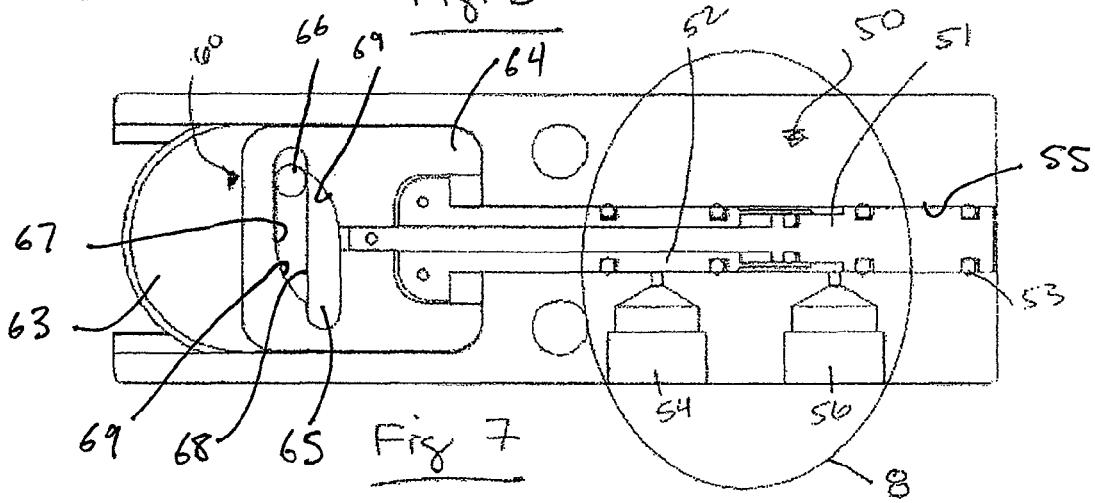
FIG. 7 is a cross-sectional view of the precision pump of FIG. 6 in a second position (P2).
Figure 8:
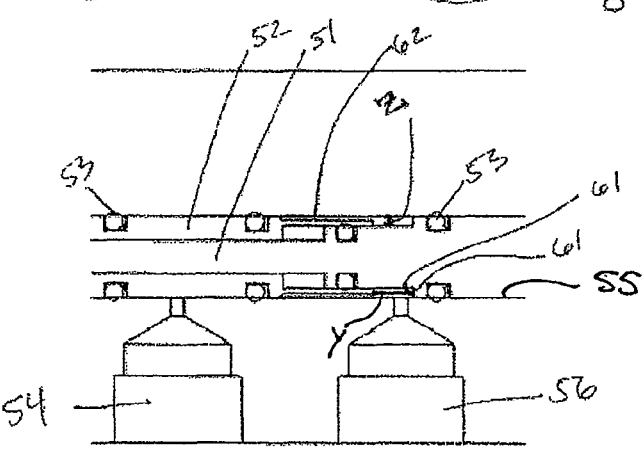
FIG. 8 is an enlarged section view taken from section 8 of FIG. 7.

FIGS. 6-11 further illustrate one example of the steps performed for pumping fluid through the precision pump 50. In FIG. 6, the pistons 51, 52 are shown in a first position (P1) where no bolus of fluid is contained within the space between the mating features 61, 62 of the pistons 51, 52. In this position (P1), the mating features 61, 62 are situated such that they are in complete contact with each other and, therefore, generally no fluid is contained between the mating features 61, 62 (see FIG. 8). In FIG. 7, the pistons 51, 52 are shown in a second position (P2) where the second piston 52 has been axially translated in a direction so that a space is formed between the mating features 61, 62. A vacuum is formed between the mating features 61, 62 which draws fluid from the inlet port 56 and fills the space between the mating features 61, 62. The outside diameter of the mating feature 61 of the first piston 51 is large enough so that the distance between the inner walls of the fluidic pathway 55 and the outside diameter of the mating feature 61 is a specified distance (shown in FIG. 8 to be dimension Z). Dimension Z can be any number of values necessary for enabling the desired volume of fluid to be transferred via annular flow between the inlet port 56 and outlet port 54. The volume of fluid transferred between the inlet port 56 and the outlet port 54 is also dependent upon the length Y (FIG. 8) of the space formed between the mating features 61, 62 (controlled by the driving mechanism), which may be any distance necessary to achieve the desired dispensing volume per stroke cycle.

Figure 9:
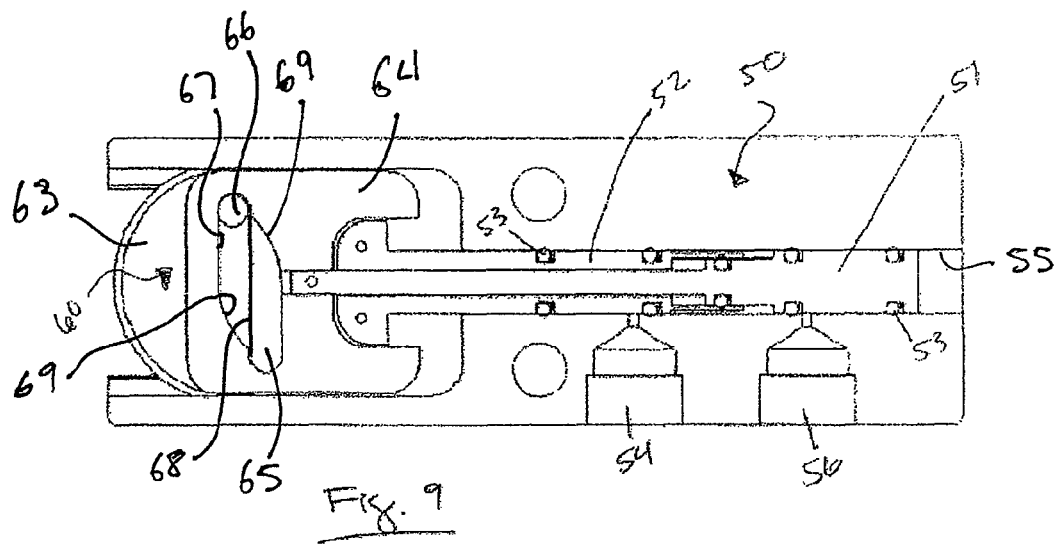
FIG. 9 is a cross-sectional view of the precision pump of FIG. 6 in a transition phase.
Figure 10:
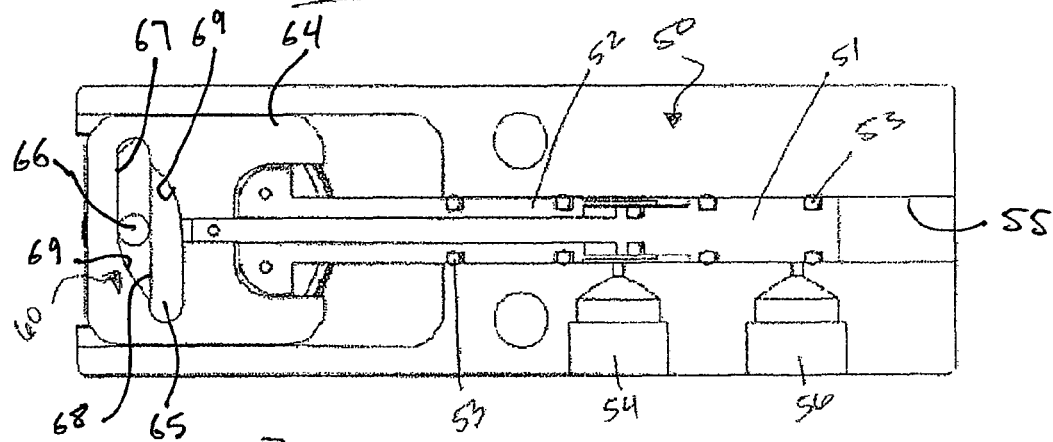
FIG. 10 is a cross-sectional view of the precision pump of FIG. 6 in a third position (P3).

The first and second pistons 51, 52 are then axially translated in concert away from the inlet port 56 and positioned so that the outlet port 54 is situated at some point between the mating features 61, 62 of the pistons 51, 52, as illustrated in FIG. 10 and referred to as the third position (P3). FIG. 9 illustrates the pistons 51 and 52 traveling in concert between P2 and P3 and specifically how during this transition there is no cross talk between the inlet port 56 and outlet port 54, thus prohibiting, or substantially prohibiting, the ability of the precision pump to free-flow fluid between its inlet port 56 and outlet port 54, except in the event of failure of one or more seals.

Figure 11:
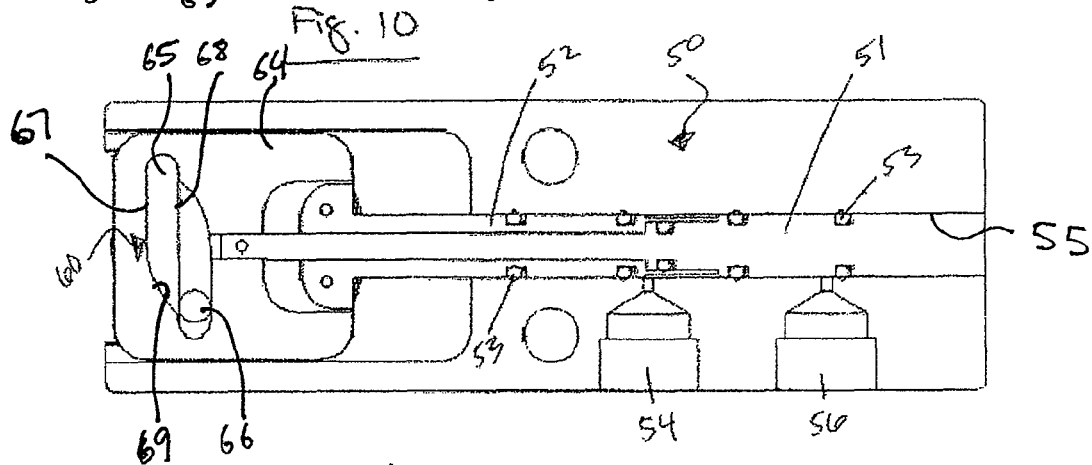
FIG. 11 is a cross-sectional view of the precision pump of FIG. 6 in a fourth position (P4).

The precision pump 50 then configures into the fourth position (P4) wherein the second piston 52 is axially translated toward the first piston 51 as the first piston 51 remains stationary until the mating features 61, 62 of the pistons 51, 52 are in complete contact, as illustrated in FIG. 11. The compression of the mating features 61, 62 forces the fluid out from the space previously formed between the mating features 61, 62 and dispenses a specified volume of fluid through the outlet port 54. Although the inlet port 56 and outlet port 54 are shown in this example to be axially aligned, they may have other linear and rotational positions relative to each other in other embodiments. After P4, the precision pump returns to P1 (again prohibiting cross talk between the inlet port 56 and outlet port 54) with the mating features 61, 62 remaining generally in full contact with each other.

Preferably, the mating features 61, 62 come into full contact when dispensing fluid from the space between them. Very little or, preferably, no fluid is contained in the space between the mating features 61, 62 as they move between position P4 and position P1. However, in other embodiments, the mating features 61, 62 can be located in a spaced relationship in position P4 and when moving between position P4 and position P1. The mating features 61, 62 preferably do not move relative to one another between positions P1 and P4 in either direction. However, small amounts of relative movement may exist during such movement in some embodiments.

The speed at which the precision pump 50 advances through a cycle (the sequential steps P1-P4) can be altered so that a desired flow rate can be achieved. Additional factors such as the size and shapes of the mating features 61, 62 and stroke length, as previously mentioned, can be tailored to best suit the requirements of the pump (e.g. flow rate, dispensing volumes, precision).

The cam system 60 illustrated in FIGS. 6-11 comprises a rotor 63, a first follower 64, and a second follower 65. A pin 66 is connected to the rotor 63 and is sized and shaped to extend through a first slot 67 in the first follower 64 and a second slot 68 in the second follower. The first follower 64 is operatively connected to the first piston 51. The second follower 65 is operatively connected to the second piston 52.

The first slot 67 and the second slot 68 each have a length extending transverse to the direction of reciprocating movement of the pistons 51, 52. For example, in FIGS. 6, 7, and 9-11, the length of slots extends generally perpendicular to the direction of reciprocating movement of the pistons 51, 52. The slots 67, 68 also have a width extending generally along the direction of reciprocating movement of the pistons 51, 52. One of the slots has a width greater than the width of the other. For example, as illustrated in FIGS. 6, 7, and 9-11, the first slot 67 can have a greater width than second slot 68. The first slot 67 illustrated in FIGS. 6, 7, and 9-11 has a width that is approximately twice the diameter of the pin 66, while the second slot 68 has a width that is close to the same size as, or slightly larger than, the diameter of the pin 66. Both of the slots 67 and 68 can have a length sufficient to allow the pin to move through its full range of motion while the rotor 63 rotates.

The slot having the greater width (first slot 67 in FIGS. 6, 7, and 9-11) can have a pair of generally opposing guide surfaces 69. The orientation of the slots and the guide surfaces 69 are configured such that as the rotor 63 moves the pin 66 within the slot (e.g. first slot 67), interaction between the pin 66 and the slots, including the guide surfaces 69, urges the one piston (e.g. first piston 51) toward or away from the other piston. For example, with reference to FIGS. 6 and 7, as the rotor 63 rotates in a counter-clockwise direction, the pin 66 moves toward and along the upper guide surface 69 while engaging a wall of the slot 68, thereby urging the second piston 52 away from the first piston 51. Conversely, with reference to FIGS. 10 and 11, as the rotor 63 rotates counter-clockwise, the pin 66 moves toward and along the lower guide surface 69 while engaging a wall of the slot 68, thereby urging the second piston 52 toward the first piston 51. Thus, interaction between the pin 66 and the slots 67 and 68 controls the movement of both the first piston 51 and the second piston 52.

The guide surfaces 69 can have a curved shape as illustrated in FIGS. 6, 7, and 9-11. For example, the curved shape of the guide surfaces 69 can correspond to the motion of the pin 66. In the embodiment illustrated in FIGS. 6, 7, and 9-11, the guide surfaces 69 generally follow an arc defined by the radially-outermost portion of the pin 66 as it moves about a rotational axis of the rotor 63.

It has been further contemplated that the precision of small volumes of fluid can additionally be accomplished with the precision pump designs described below. FIGS. 12-28 and 30-46 illustrate additional exemplifying embodiments of precision pumps. Some embodiments of precision pumps do not rely on annular flow, and instead rely on volume displacement that occurs within a cavity formed within the piston, for example. By filling and dispensing volumes of fluid within a cavity formed within a piston, shorter piston strokes can be used to transfer fluid between the inlet and outlet port. Therefore, in some embodiments, smaller and more compact fluid pumps can be produced, which is beneficial in several applications (e.g. wearable drug delivery systems, PCA's (patient-controlled analgesia)).

Second Exemplifying Embodiment of a Precision Pump

Figure 12:
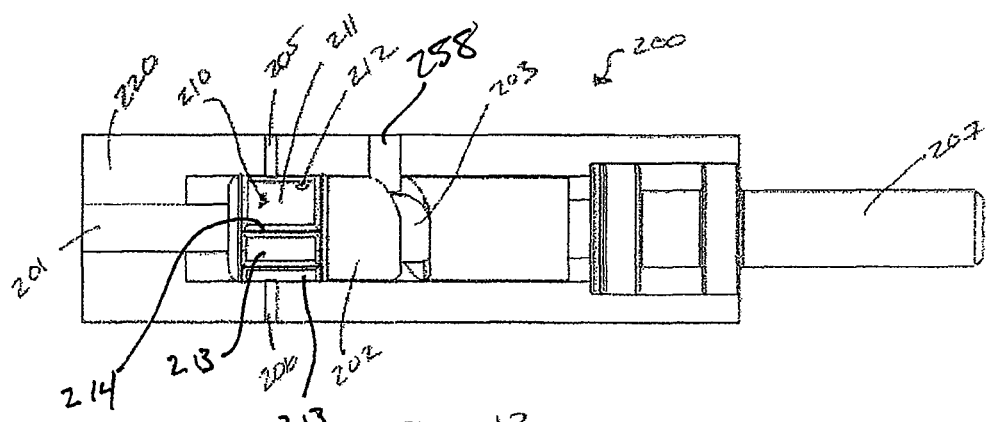
FIG. 12 is a partial cross-sectional side view of a precision pump with a piston that both rotates and axially translates, according to an embodiment.
Figure 13:
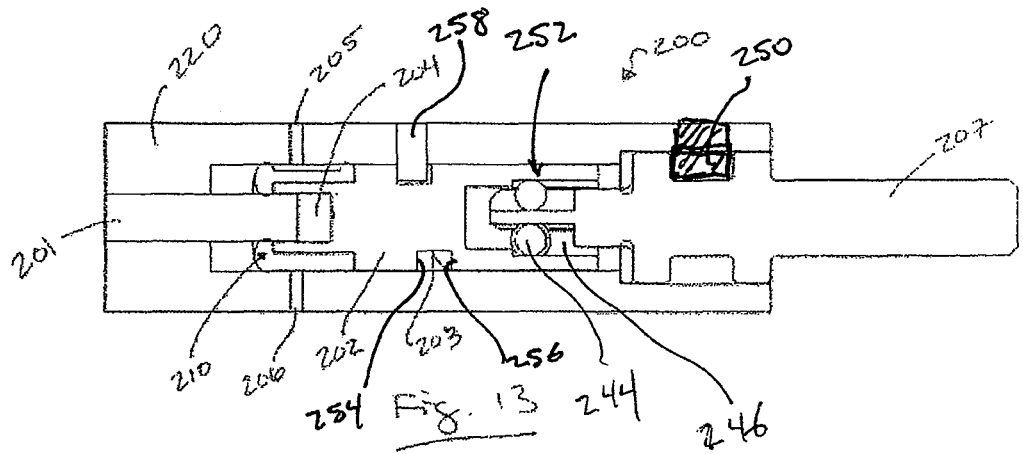
FIG. 13 is a full cross-sectional view of the precision pump of FIG. 12.

FIGS. 12 and 13 illustrate an exemplifying embodiment of precision pump 200. Precision pump 200 is a volume displacement pump wherein a cavity 204 is formed between a pin 201 and a piston 202. A barrel cam feature 203 positioned at one end of or along the piston 202 controls the linear translation of the piston 202 along its central axis. Although shown in this embodiment as having a barrel cam 203 which assists in controlling the linear translation of the piston 202 along its central axis, other driving mechanisms can be implemented in some embodiments. As the piston 202 axially travels away from the pin 201, a cavity 204 is formed. Fluid from the inlet port 205 can then fill the cavity 204. The axial translation of the piston 202 determines the size of the cavity 204, and thus the volume of fluid which will be transferred from the inlet port 205 to the outlet port 206.

The pin 201 can be fixedly attached to a pump housing 220, as illustrated in FIGS. 12 and 13. In some embodiments, the pin 201 can be movable relative to the housing 220, for example as described below in connection with FIGS. 30-31 and 38-39.

By way of example only and as illustrated in FIGS. 12 and 13, rotation of a motor or input shaft 207 (which is coupled to the piston 202) can be transferred the to the piston 202. The barrel cam 203 can urge axial translation of the piston 202 as the piston 202 rotates. During one complete revolution of the motor shaft 207 of the embodiment of FIGS. 12 and 13, the piston 202 axially and rotationally travels which allows fluid to fill the cavity 204 from the inlet port 205 and subsequently dispense the fluid out the outlet port 206. In some embodiments, the piston 202 axially and rotationally travels allowing fluid to fill the cavity 204 from the inlet port 205 and subsequently dispense the fluid out the outlet port 206 during more or less than one complete revolution of the motor shaft 27. For example, the ratio of rotations of the shaft 207 to the piston 202 can be varied by appropriate gearing.

The motor or input shaft 207 can be coupled to any drive mechanism of suitable speed and torque. For example, the input shaft 207 can be connected to a foot pump, stepper motor, DC motor or other single or variable speed motor.

In the embodiment illustrated in FIGS. 12 and 13, a sliding coupler 252 connects the motor or input shaft 207 to the piston 202. The sliding coupler 252 allows the piston 202 to move relative to the input shaft 207 generally along an axis of rotation of the input shaft 207. The sliding coupler 252 comprises a plurality of balls 244 positioned in grooves 246 that extend generally parallel to the axis of rotation. Grooves 246 are located in both the input shaft 207 and the piston 202. Therefore, the balls 244 can roll within the grooves 246 to allow axial movement of the piston 202 relative to the input shaft 207 and can transmit rotational movement of the input shaft 207 to the piston 202. Other sliding couplers of other types and configurations, such as those described below and shown in connection with other embodiments, can be substituted or for the sliding coupler 207 in the embodiment of FIGS. 12 and 13 and can be employed in other embodiments.

A retainer 250 can be used to restrict, limit, or impede movement of the input shaft 207 relative to the housing 220, for example as in the embodiment of FIGS. 12 and 13. The retainer 250 can be a pin, collar, ring or other device now know to those of skill in the art or later developed.

Figure 14:
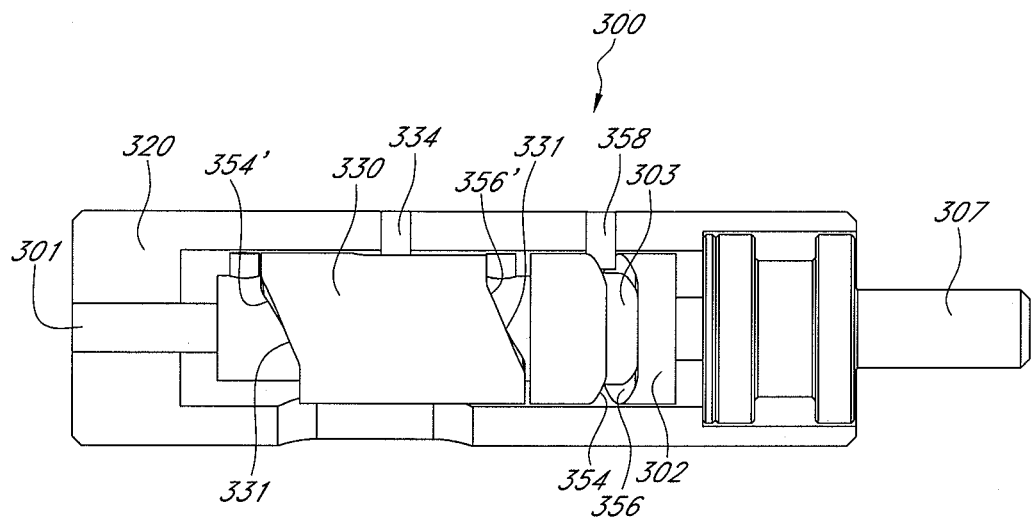
FIG. 14 is a partial cross-sectional side view of a precision pump comprising a plurality of cams and o-ring seals, according to an embodiment.
Figure 15:
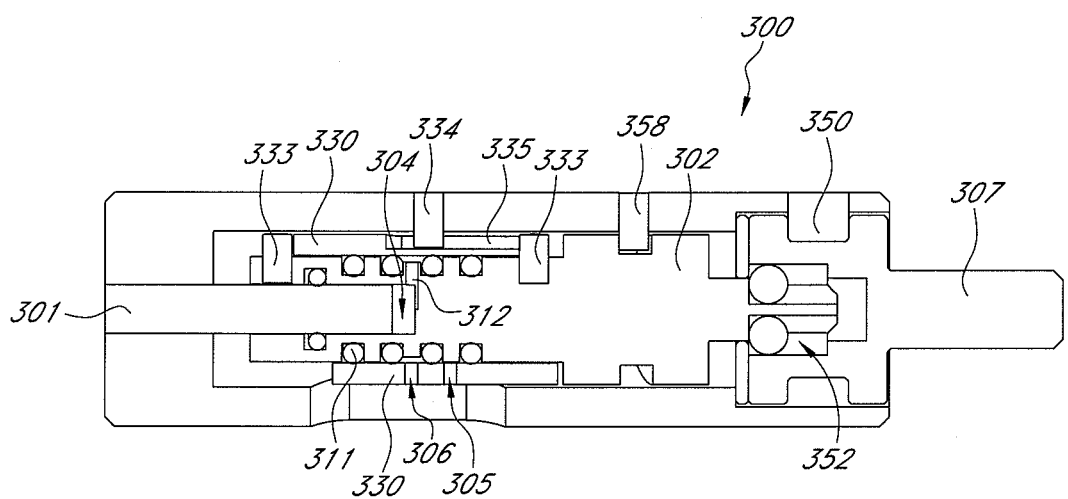
FIG. 15 is a full cross-sectional view of the precision pump of FIG. 14.

The barrel cam 203 can comprise a pair of generally opposing guide surfaces 254, 256. In the embodiment illustrated in FIGS. 12, and 13, a pin 258 is fixedly attached to and extends from the housing 220 into a space between the guide surfaces 254, 256. As the piston 202 rotates it is urged generally along the pin 201 by engagement of the pin 258 against the guide surfaces 254, 256. In some embodiments, such as that illustrated in FIGS. 12 and 13, a single pin 258 can alternately engage the guide surfaces 254, 256. In other embodiments, more than one pin can engage the guide surfaces 254, 256. For example, one pin can engage a first guide surface 254 and a second pin can engage a second guide surface 256. Such an arrangement is shown in FIGS. 14 and 15, described in greater detail below in connection with the valving cam 330. In some embodiments, the piston can be moved longitudinally without being rotated while the pin(s) are rotated about the piston, as also described in greater detail in connection with the valving cam 330, shown in FIGS. 14 and 15.

Although illustrated as a single component in FIGS. 12 and 13, the piston 202, the barrel cam 203, or both can be formed as one or multiple components in some embodiments.

A valve seal 210 is shown in this example and controls the ability of the fluid to enter the cavity 204 from the inlet port 205 and dispense from the cavity 204 through the outlet port 206 by restricting fluid communication about the piston 202. Although the custom fluidic seal 210 is shown in this embodiment to have a specific custom configuration, other custom fluidic seals can be implemented into the precision pump 200 in some embodiments. The valve seal 210 shown in this embodiment has a first pocket 211 with a fluid pathway 212 so that when the first pocket 211 is exposed to either the inlet port 205 or outlet port 206, fluid is allowed to travel in and out of the cavity, respectively. Additional pockets 213 around the outer circumference of the valve seal 210 assist in reducing friction along the inner walls of the housing 220 as the valve seal 210 rotates along with the piston 202 (compared to a seal without pockets and wherein the portions of the seal other than the first pocket 211 are sized to engage the inner surface of the housing 220. In some embodiments, such as that illustrated in FIGS. 12 and 13, the seal 210 can comprise ribs or protrusions 214 between the pockets that are configured to inhibit fluid flow as the piston 202 rotates. Although the illustrated ribs or protrusions 214 have a generally straight configuration, other configurations can be used in some embodiments.

Third Exemplifying Embodiment of a Precision Pump

FIGS. 14 and 15 illustrate a precision pump 300, which is another embodiment of a volume displacement pump wherein a cavity 304 is formed between a pin 301 and a piston 302. The illustrated precision pump 300 is similar to the illustrated precision pump 200 in some respects, thus similar reference numerals are used in connection with the precision pump 300 to designate components that are similar to those of other precision pumps described herein, such as the precision pump 200. Thus, rather than repeat the description of similar components, it should be understood that the description of similar components herein also can also apply to the similarly numbered components of this embodiment. The illustrated precision pump 300 is different from the precision pump 200 and other precision pumps disclosed herein in some respects, such as those noted below.

Like the precision pump 200, the precision pump 300 includes a barrel cam feature 303 along the piston 302 so that when the motor shaft 307 (which is coupled to the piston 302) rotates, the piston 302 is translated along its center axis, as described above. Although shown in this embodiment as having a barrel cam 303 which assists in controlling the linear translation of the piston 302 along its central axis, other driving mechanisms can be implemented in some embodiments. A valving cam 330 of this embodiment of the precision pump 300 is designed and configured such that the valving cam 330 can axially translate at a pace and distance separate from that of the piston 302. In some embodiments, such as that illustrated in FIGS. 14 and 15, this allows a significantly shorter piston 302 stroke and valving cam 330 stroke necessary for the filling and dispensing of fluid within the cavity 304 formed within the piston 302 (compared to the precision pump 200, for example).

As shown best in FIG. 14, the valving cam 330 has placement features 331, such as guide surfaces 354', 356', along its proximal and distal ends which interact with pins 333 extending from the piston 302 such that when the piston valve 302 rotates, the pins 333 extending from the piston 302 interact with the proximal and distal placement features 331 which cause the valving cam 330 to translate along its central axis. A pin 334 extending from the housing 320 into a slotted feature 335 of the valving cam 330 restricts the valving cam 330 from rotational movement and allows the valving cam 330 to only axially translate as the pin 334 travels along the slotted feature 335 of the valving cam 330. Although the valving cam 330 is illustrated as having proximal and distal placement features 331 and slotted feature 335 to control its linear and non-rotational movement, any features and associated features on surrounding parts can be implemented into the precision pump 300 to control the movement of the valving cam 330 in some embodiments.

The precision pump 300 transfers fluid between its inlet port 305 and outlet port 306 as the piston 302 rotates and axially translates along its central axis. As the piston 302 rotates, the piston fluid pathway 312 is aligned with an inlet port 305, an outlet port 306, or a fluidic seal 311 which inhibit fluid from traveling out from or into the piston 302. Fluidic seals 311 are placed at select positions throughout the precision pump in order to contain and control the flow of the fluid within the precision pump 300 and other numbers of fluidic seals can be used in some embodiments.

As the piston 302 and extending pins 333 rotate and engage placement features 331 on the valving cam 302, the valving cam 302 is axially translated which enables the alignment of the outlet port 306 or inlet port 305 with the fluid pathway 312 of the piston 302. When the outlet port 306 of the valving cam 330 is aligned with the fluid pathway 312 of the piston 302, the fluid contained within the cavity 304 formed in the piston 302 is allowed to dispense out the outlet port 306. The axial translation of the piston 302 in the direction of the pin 301 collapses the cavity 304 assists in forcing the fluid contained within the cavity 304 to dispense out the outlet port 306. Similarly, when the inlet port 305 of the valving cam 330 is aligned with the fluid pathway 312 of the piston 302, fluid is able to fill the cavity 304 formed within the piston 302. The axial translation of the piston 302 away from the pin 301 forms the cavity 304 and assists in allowing fluid to fill the cavity 304 from the inlet port 305.

Fourth Exemplifying Embodiment of a Precision Pump

Figure 16:
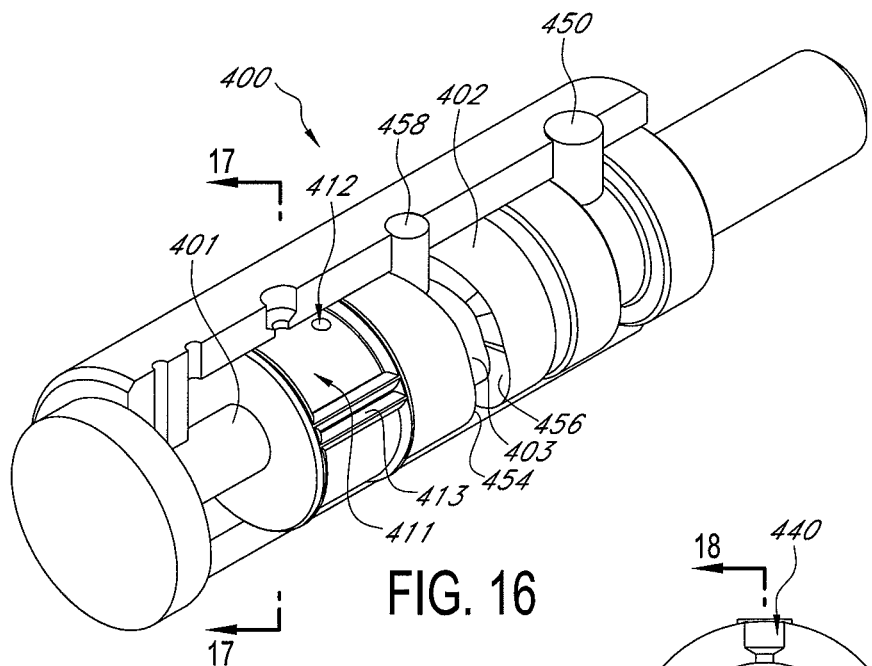
FIG. 16 is an isometric view of a precision pump with multiple inlets and a single outlet, according to an embodiment.
Figure 17:
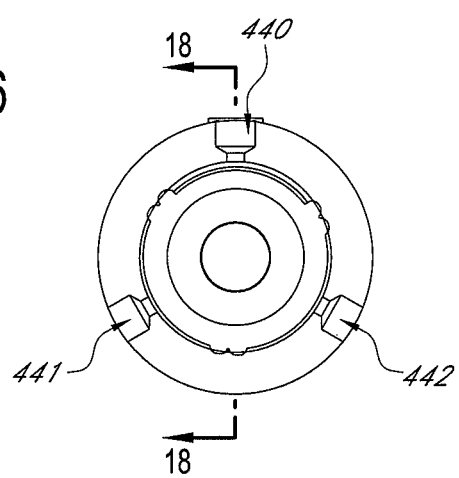
FIG. 17 is a cross-sectional view of the precision pump of FIG. 16 along line 17-17.
Figure 18:
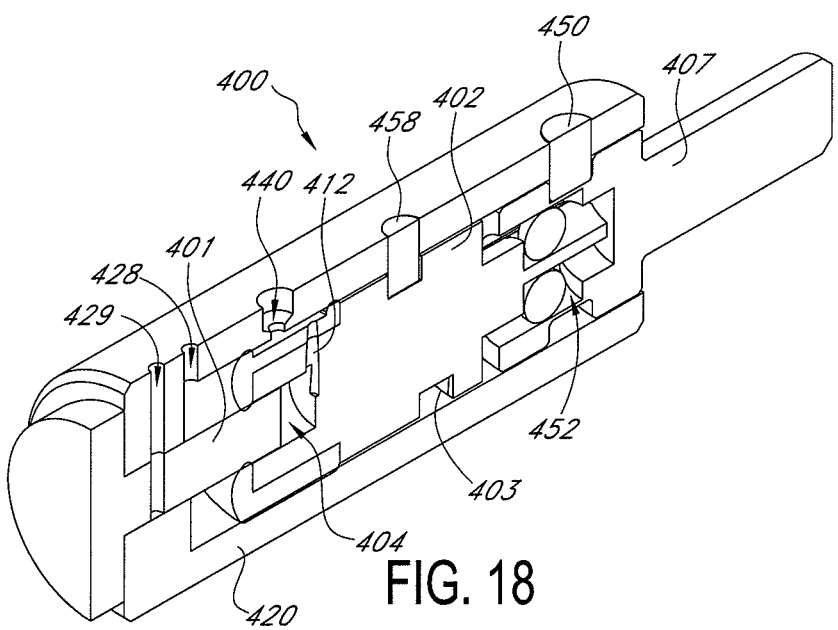
FIG. 18 is a cross-sectional view of the precision pump of FIG. 16, along line 18-18, shown in FIG. 17.

FIGS. 16-18 illustrate another embodiment of a precision pump 400. The precision pump 400 is a volume displacement pump wherein a cavity is formed between a pin 401 and a piston 402. The illustrated precision pump 400 is similar to the illustrated precision pumps 200 and 300 in some respects, thus similar reference numerals are used in connection with the precision pump 400 to designate components that are similar to those of other precision pumps described herein, such as the precision pumps 200 and 300. Thus, rather than repeat the description of similar components, it should be understood that the description of similar components herein also can also apply to the similarly numbered components of this embodiment. The illustrated precision pump 400 is different from the precision pump 200 and other precision pumps disclosed herein in some respects, such as those noted below.

A barrel cam feature 403 at one end or along the length of the piston 402 controls the linear translation of the piston 402 along its central axis. Although shown in this embodiment as having a barrel cam 403 which assists in controlling the linear translation of the piston 402 along its central axis, other driving mechanisms can be implemented in some embodiments. As the piston axially travels away from the pin 401, a cavity 404 is formed. As illustrated in FIGS. 17 and 18, the precision pump 400 can include more than one inlet port 440, 441 for enabling the addition of more than one type of fluid to enter through different inlet ports and fill the cavity 404 (best shown in FIG. 17). Once the fluids are contained within the cavity 404, the fluids are able to mix and subsequently dispense out of the outlet port 442. Although precision pump 400 is shown as having two inlet ports and a single outlet port, other numbers of inlet ports and outlet ports may be incorporated into the system in some embodiments.

The axial translation of the piston 402 determines the size of the cavity 404, and thus the volume of fluid which will be transferred from each of the inlet ports 440, 441 to at least one of the outlet ports 442. By way of example only and as illustrated in FIG. 18, rotation of the motor or input shaft 407 (which is coupled to the piston 402) can be transferred to the to the piston 202. The barrel cam 403 can urge axial translation of the piston 402 as the piston 402 rotates. During one complete revolution of the motor shaft 407, the piston 402 axially and rotationally travels. As the piston 402 axially and rotationally travels, the fluid pathway 412 in the valve seal 410 is aligned with each of the inlet ports 440, 441 and outlet port 442. Various fluids are allowed to enter the cavity 404 as the fluid pathway 412 is aligned with each of the inlet ports 440, 441. The various fluids are able to mix while contained in the cavity and then subsequently dispensed out of the outlet port 442 when the fluid pathway 412 is aligned with the outlet port 442. The filling and dispensing of the cavity 404 is in part due to the axial translation of the piston 402.

The amount of fluid drawn into the cavity 404 from each of the inlet ports 440, 441 can be varied to meet the desired volume ratios of fluids to be mixed within the cavity 404. The amount of fluid drawn into and dispensed from the cavity 404 can be varied by adjusting the profile of the guide surfaces 454, 456. For example, greater deviations of the tangent of the guide surface from perpendicular to the axis of rotation of the cam 403 over the portion of the cam 403 that interacts with the pin 458 during alignment of the pocket 411 with an input or output can result in larger draws into or dispensings from the cavity 404.

Figure 18A:
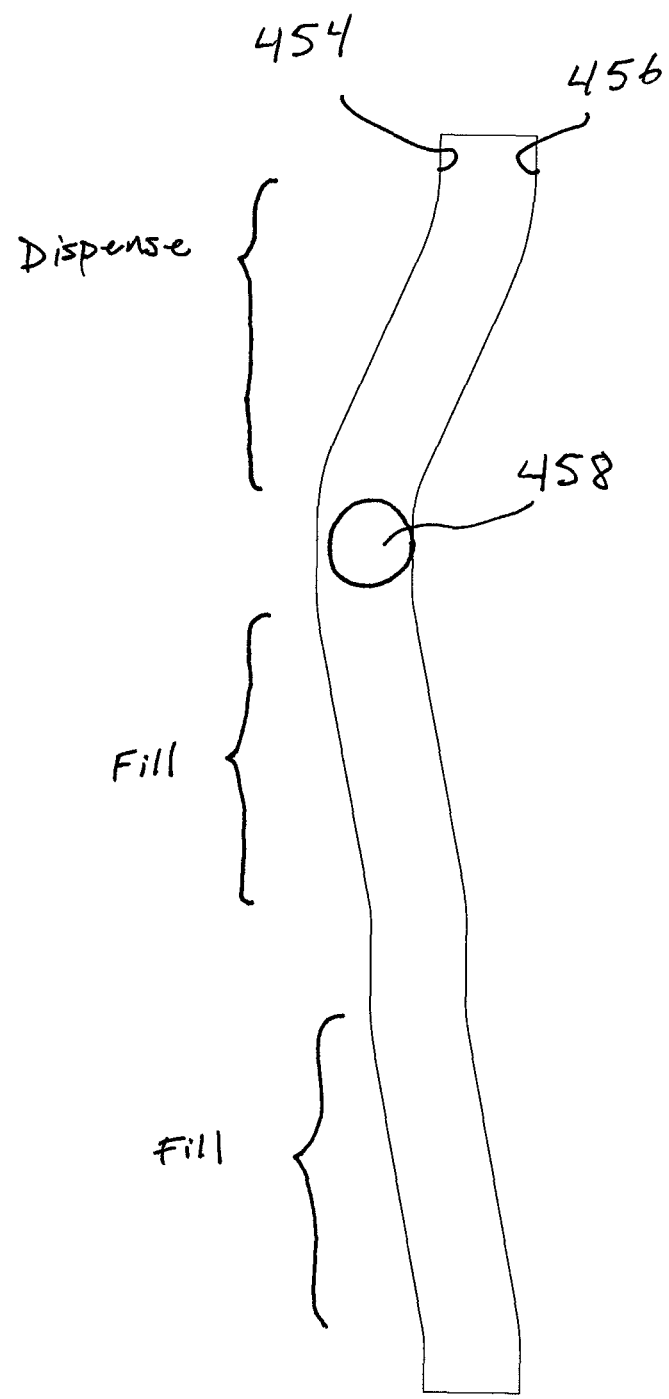
FIG. 18A illustrates the profiles of a pair of guide surfaces of the precision pump of FIG. 16.

FIG. 18A illustrates exemplifying profiles of guide surfaces 454, 456. The profiles of the guide surfaces are represented in FIG. 18A as though the guide surfaces, which extend around the circumference of barrel cam 203, were laid flat. Thus, the guide surfaces 454, 456 appear in FIG. 18A to have ends, when in fact they are continuous (in the illustrated embodiment).

The guide surfaces 454, 456 of FIG. 18A are configured to draw fluid into the cavity 404 from two inlets and dispense fluid through one outlet. Where the pin 458 interacts with the vertical portions (as FIG. 18A is oriented) of the guide surfaces, fluid is neither drawn into nor dispensed from the cavity 404. These vertical portions correspond to orientations of the seal 410 and piston 402 where the first pocket 411 is in fluid communication with no outlet or inlet. When the first pocket 411 and fluid pathway 412 are in fluid communication with an inlet or outlet, fluid can be drawn into or dispensed from the cavity. The rate of fluid draw or dispensation is influenced by the deviation of the tangent of the guide profile from vertical (again, as FIG. 18A is oriented). A greater deviation from vertical causes the piston 402 to translate axially more rapidly as the pin 458 moves over that portion of the guide surface 454, 456. Therefore, the amount of fluid drawn into or dispensed from any port can be determined by alteration of the profile of the guide surface over that portion of the guide surfaces that interacts with the pin 458 when the fluid pathway is in fluid communication with that port. Thus, the amount and rate of transfer of fluid between inputs and outputs can be programmed by the profile of the guide surfaces 454, 456.

Preferably, the pin 458 engages only one of the guide surfaces 454, 456 at a time. Thus, although the spacing between the guide surfaces is shown to be generally constant in FIG. 18A, other configurations can result in the same translation of the piston 402 as it rotates. In some embodiments, a constant or generally constant spacing between the guide surfaces, for example as shown constant in FIG. 18A, can allow the transfer rate of fluid in forward and reverse operation of the pump to be the same or substantially the same. In some embodiments, the spacing between the guide surfaces can vary along the guide surfaces such that forward and reverse operation of the pump transfer fluid at different rates.

Although shown in this embodiment to have a single outlet port 442, the precision pump 400 can have more than one outlet port. A precision pump 400 with more than one outlet port can be configured or controlled so that various volumes are dispensed from each of the outlet ports which can be useful in a number of different applications (e.g. biologics assays, laboratory analysis).

The housing 420 can comprise a passage 428 to permit venting of the housing. Venting the housing can, in some embodiments, prevent or inhibit pressure from developing within the housing that would interfere with the desired movement of the piston 402.

The pin or plunger 401 can be fixed to the housing 420 by a rod or screw advanced through the hole 429.

Fifth Exemplifying Embodiment of a Precision Pump

Figure 19:
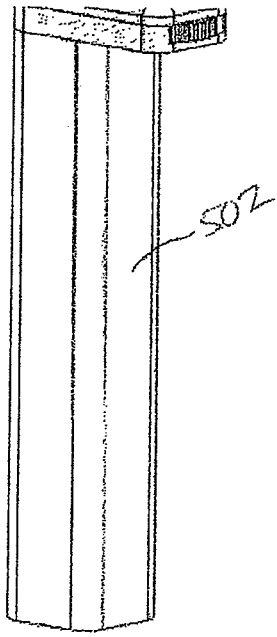
FIG. 19 is an isometric view of a precision pump adapted to a reservoir or collapsible cavity and cartridge, according to an embodiment.
Figure 20:
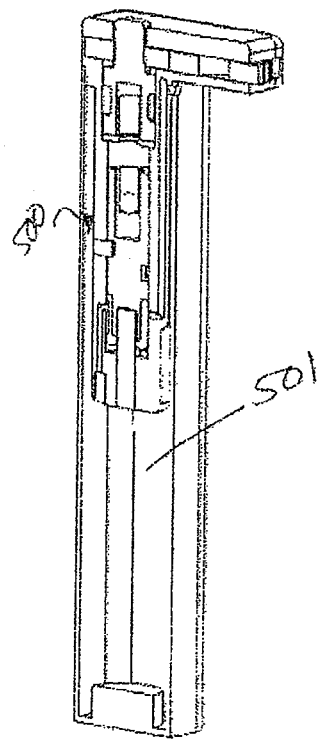
FIG. 20 is a cross-sectional view of the precision pump of FIG. 19.

FIGS. 19 and 20, illustrate one embodiment of a precision pump 500 adapted to a reservoir 501 and implemented into a disposable cartridge 502. Any of the precision pumps disclosed herein can be adapted to a reservoir without departing from the scope of the present invention. Additionally, more than one reservoir can be adapted to an embodiment of a precision pump without departing from the scope of the present invention. The reservoir(s) can be vented or can comprise a collapsible chamber to facilitate the drawing of fluid from the reservoir.

The precision pump and adapted fluid reservoir(s) can then be assembled as the disposable sub-assembly to a non-disposable sub-assembly. The precision pumps disclosed herein make an optimal choice for composing at least part of a disposable device due to their small number of inexpensive parts. Furthermore, the reservoir allows a large amount of fluid to be directly transferred through the precision pump, which can be easily removed when emptied (along with the precision pump) and replaced with a new reservoir and precision pump. Therefore, a large amount of fluid can be delivered from a compact device, which is in part due to the short travel requirements of the precision pump that retrieves and dispensed highly precise volumes of fluid consistently over essentially the lifetime of the precision pump. The precision pumps disclosed herein thus provide significant advantages to the prior art and can be implemented in any number of applications that can benefit from the characteristics of the precision pumps described and contemplated.

Sixth Exemplifying Embodiment of a Precision Pump

All of the features and embodiments disclosed herein can be manually or programmably operated and are adjustable (scaled) to dispense any size of volumes necessary. Furthermore, the fluid delivery devices disclosed herein can be used and/or implemented into any number of systems for the delivery of fluids (e.g. biologics, fuel), and not solely for the delivery of medication and/or drugs. The fluid delivery systems can also be implemented into hand-held delivery devices (e.g. insulin dispensing pen as shown by way of example in FIGS. 21 and 22) and wearable devices, as discussed above.

Figure 21:
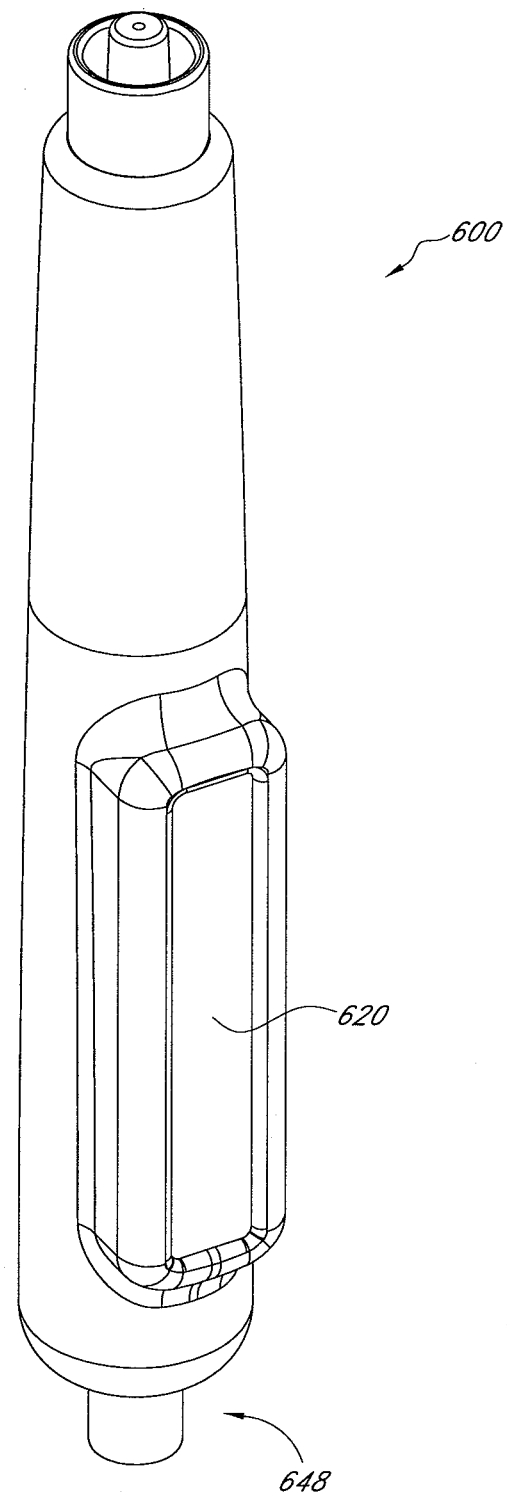
FIG. 21 is an isometric view of a precision pump incorporated into a hand-held dispensing pen according to an embodiment.
Figure 22:
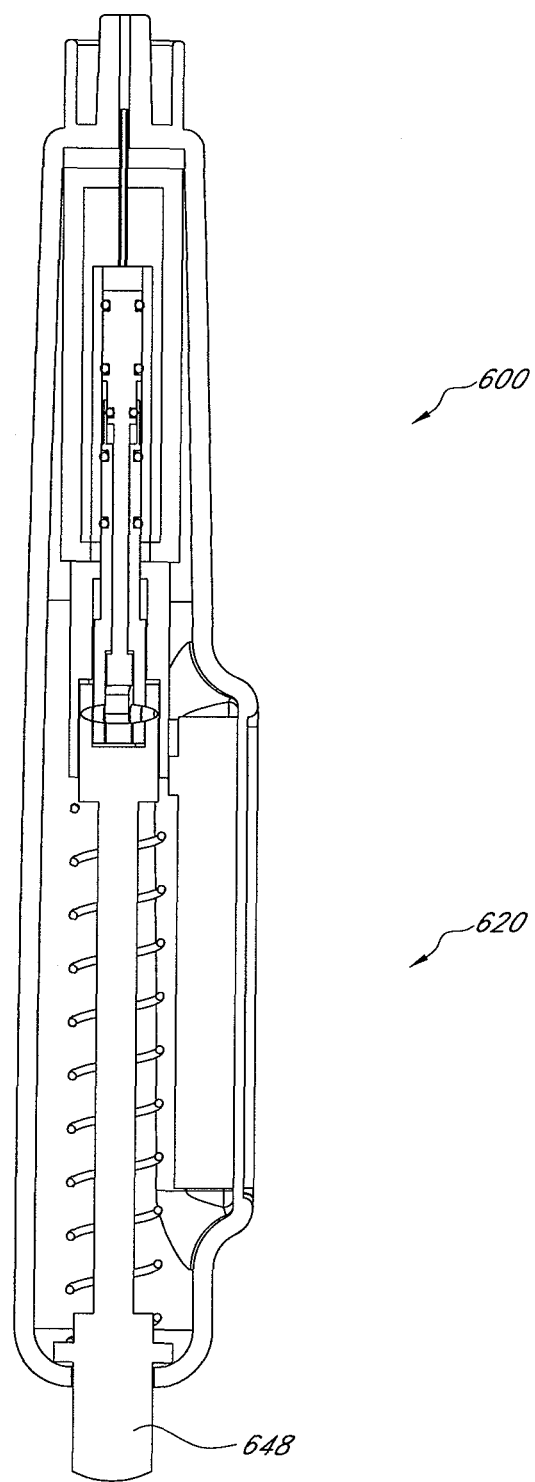
FIG. 22 is a cross-sectional view the precision pump of FIG. 21.
Figure 23:
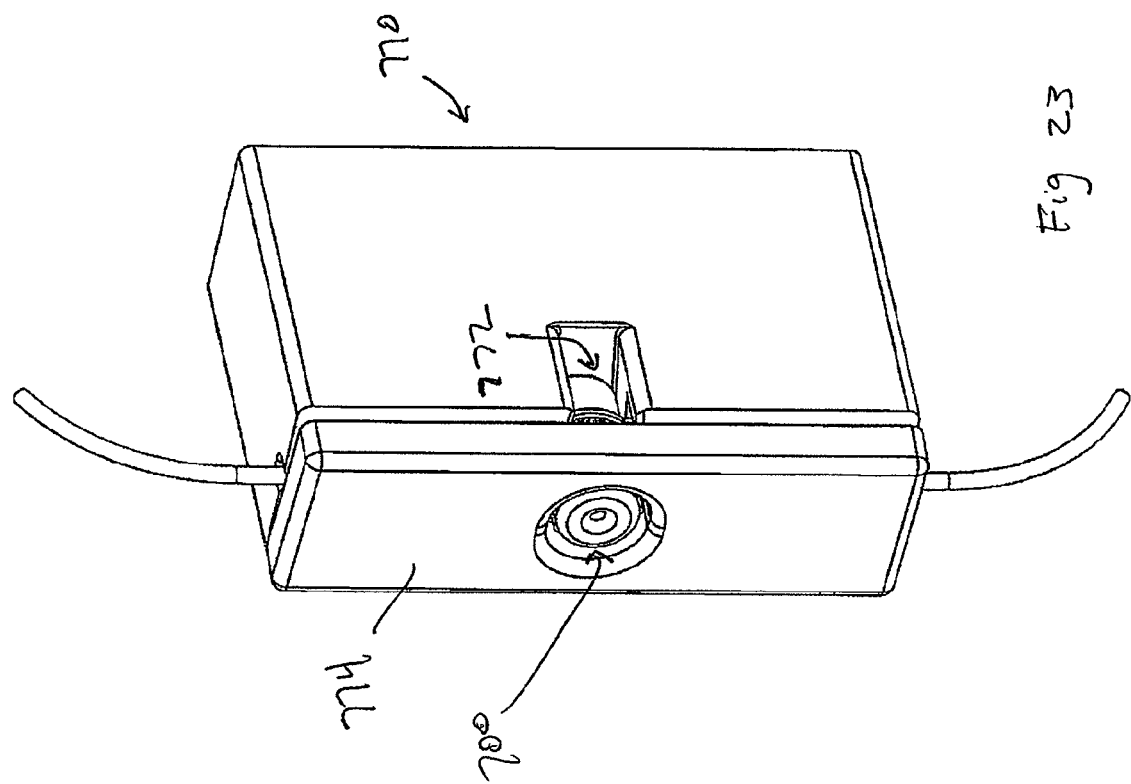
FIG. 23 is an isometric view of a precision pump that can comprise a disposable pump assembly and a durable drive system, according to an embodiment.

FIGS. 21 and 22 illustrate a precision pump 600, which is implemented in a hand-held insulin dispensing pen. The illustrated precision pump 600 is similar to the illustrated precision pump 50 in some respects, thus similar reference numerals are used in connection with the precision pump 600 to designate components that are similar to those of the precision pump 50, described above. Thus, rather than repeat the description of similar components, it should be understood that the description of similar components herein also can also apply to the similarly numbered components of this embodiment. The illustrated precision pump 600 is different from the precision pump 50 in some respects. For example, the precision pump 600 comprises a manual actuator 648.

Seventh Exemplifying Embodiment of a Precision Pump

FIGS. 23-28 illustrate another embodiment of a precision pump 700. The precision pump 700. The illustrated precision pump 700 is similar to other illustrated precision pumps described herein in some respects, thus similar reference numerals are used in connection with the precision pump 700 to designate components that are similar to those of other precision pumps described herein. Thus, rather than repeat the description of similar components, it should be understood that the description of similar components herein also can also apply to the similarly numbered components of this embodiment. The illustrated precision pump 700 is different from the other precision pumps disclosed herein in some respects, such as those noted below.

The precision pump 700 can form a portion of a pumping system such as an infusion pump. The pumping system can further comprise a drive module 770. Expensive drive components and controls can be placed in the drive module with a durable housing. On the other hand, the precision pump 700 can be inexpensively manufactured so as to be disposable in some embodiments. Thus, the cost of the system can be reduced by reusing the more costly drive components, while replacing the relatively inexpensive pump components.

Figure 24:
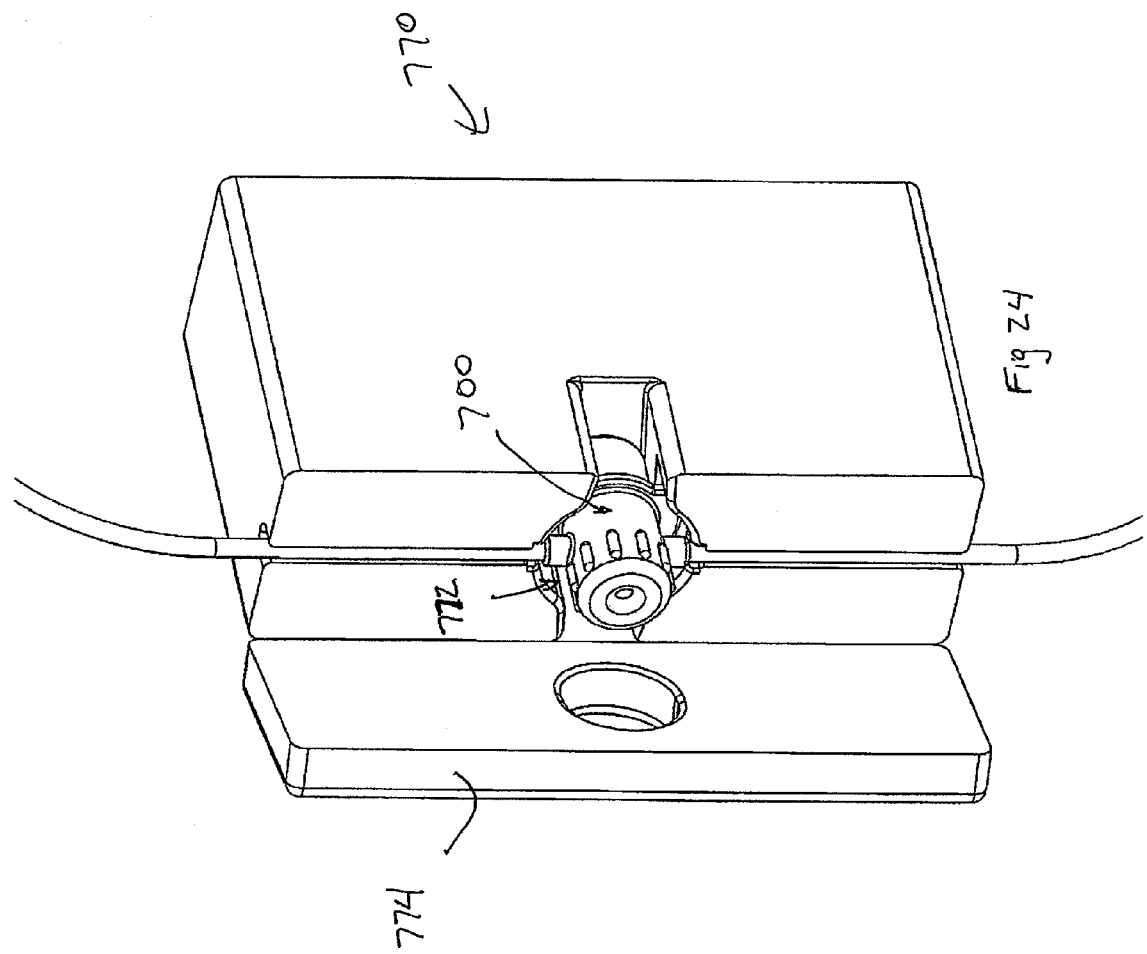
FIG. 24 is an isometric view of the precision pump of FIG. 23 with a cover of a drive housing in an opened position.
Figure 25:
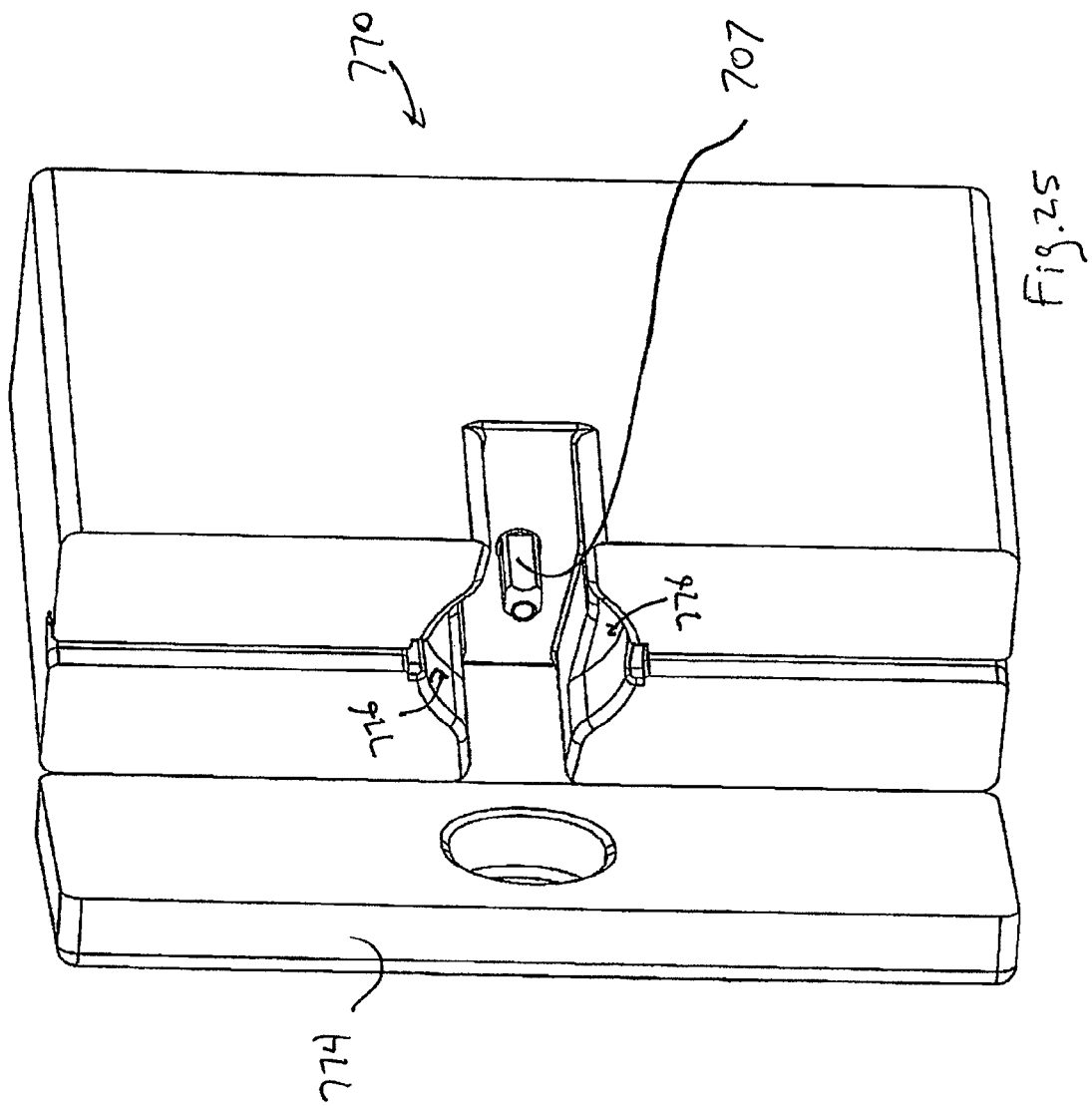
FIG. 25 is an isometric view of the drive housing of the precision pump of FIG. 23 with a pump assembly removed.
Figure 26:
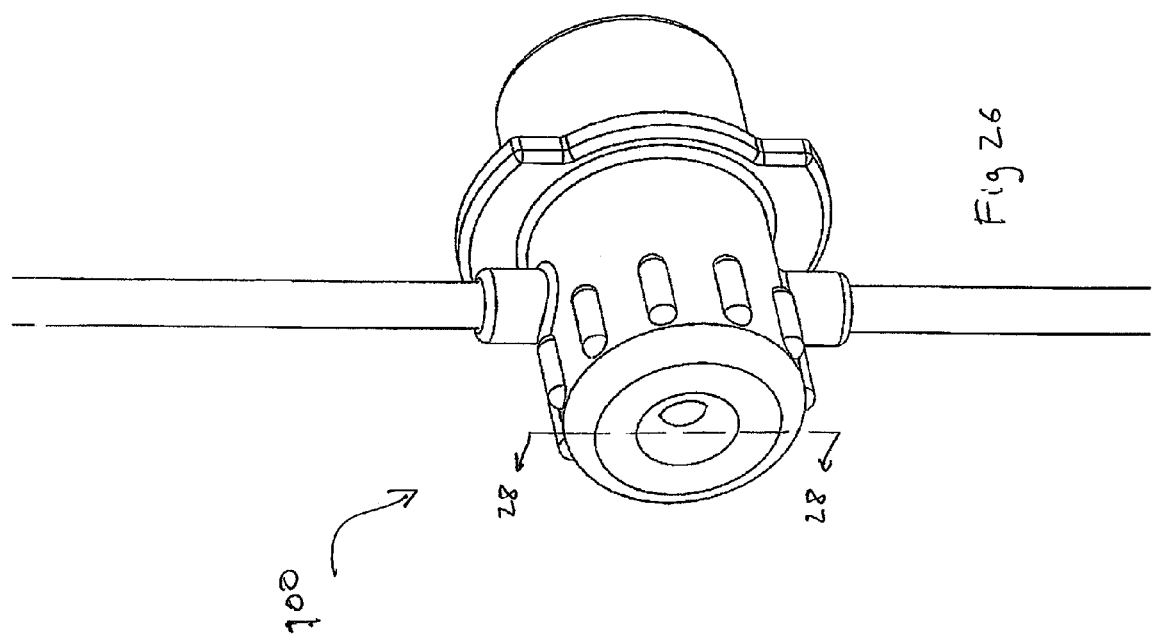
FIG. 26 is a front isometric view of the pump assembly of the precision pump of FIG. 23.
Figure 27:
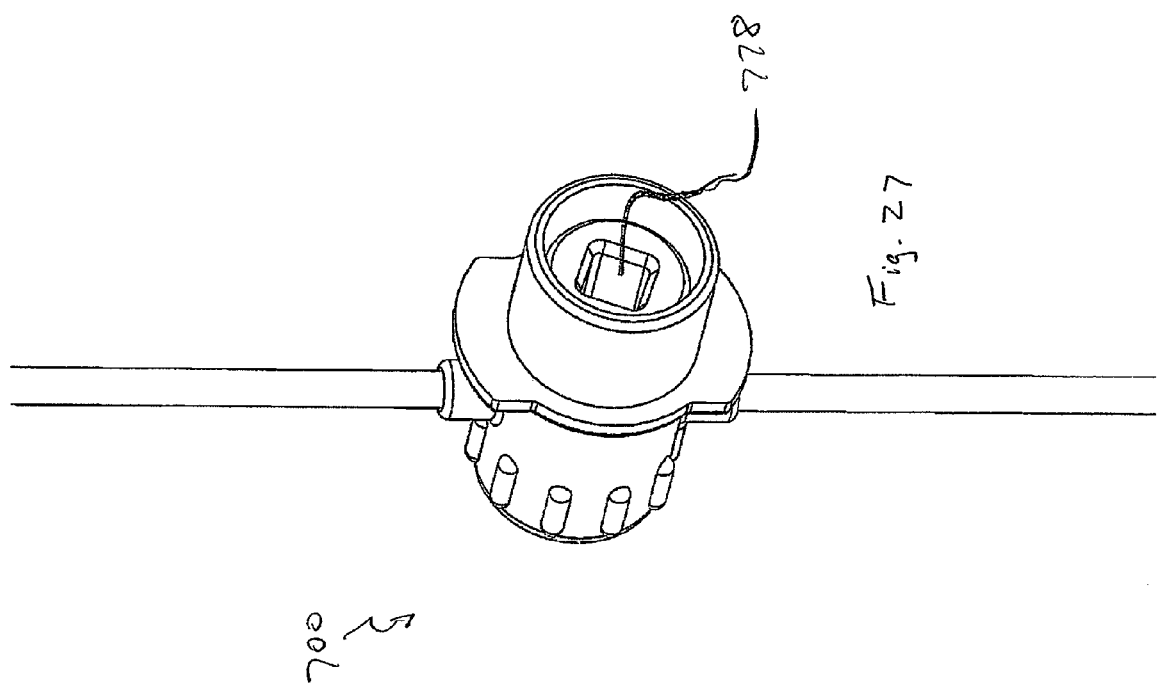
FIG. 27 is a rear isometric view of the pump assembly, shown in FIG. 26, of the precision pump of FIG. 23.

As illustrated in FIGS. 24 and 25, the drive module 770 can comprise a recess 772 sized and shaped to receive the pump 700. The drive module 770 can further comprise a retainer 774 configured to keep the pump 700 engaged with the drive module and properly connected to a drive shaft 707. Although the retainer 774 is illustrated as a door or cover, the retainer can have other configurations in some embodiments. For example, the retainer can comprise projections from a housing of the drive module located within the recess 772 and configured to engagingly retain the pump 700 within the recess.

The pump 700 and the drive module 770 are preferably configured to prevent rotation of the pump relative to the drive module. For example, in the embodiment illustrated in FIGS. 24-26, the pump comprises a pair of protrusions, shaped generally as flanges, which mate with a pair of similarly shaped recesses 776 in the drive module. As an additional example, the shapes of the exterior of the pump 700 and the recess 772 can have a shape other than that of a cylinder with a circular cross section so that the exterior of the pump 700 is prevented from rotating with respect to the drive module 770 by interference between the pump 700 with the recess 772.

The pump 700 can comprise a receptacle 778 configured to receive the drive shaft 707. Alternatively, the pump can comprise a shaft that extends into a receptacle in the drive module 707. The shaft and the receptacle are sized and shaped to transfer rotational motion from the drive module to the pump. This can generally be accomplished by providing the shaft and receptacle with sizes and shapes that are (1) mating and non-circular in cross section, (2) eccentric to the axis of their rotation, or both (1) and (2). For example, in the embodiment illustrated in FIGS. 27 and 28, the drive shaft 707 and the recess 778 sized and shaped for mating engagement and each have a square cross section. Other types of couplings between the durable housing containing the drive mechanism and the disposable pump can be incorporated into some embodiments.

The interface between the drive module and the pump can be accomplished by a simple sliding coupling. The drive shaft 707 and the receptacle 778 can be permitted to slide relative to each other along their axis of rotation during operation of the pump system.

The precision pump 700 is a volume displacement pump wherein a cavity is formed between a pin 701 and a piston 702. As noted above, volumetric displacement provides high precision and accuracy of fluid delivery. In some embodiments, sensors can be incorporated, such as, for example, pressure or flow sensors. In the embodiment shown in FIG. 28, a sensor 727 is positioned in the piston 702 between the cavity 704 and the recess 778 and is in fluid communication with the cavity 704. When the cavity 704 is in fluid communication with the inlet port 705, the sensor can sense the upstream pressure in the inlet port 705 and the passage connected thereto. Similarly, when the cavity 704 is in fluid communication with the outlet port 706, the sensor can sense the downstream pressure in the outlet port 706 and the passage connected thereto. Thus, the system could be made to be closed loop and, as such, self-correcting, thereby improving further accuracy of delivery.

For example, a signal from the sensor 727 can be communicated, by wired or wireless communication, to a control system. The control system can be configured to receive and process the signal from the sensor, and adjust actuation of the pump automatically, notify a pump operator of a condition, or both.

Information provided by the sensor can, for example, allow adverse conditions to be detected. Adverse conditions that can be detected include, for example, occlusions, restricted flow, and air in the passage. When adverse conditions are detected an alarm or other notification can be communicated to an appropriate individual by, for example, via visible or audible means. Other conditions that can be detected include, for example, a reservoir or other container being empty or full. Detection of an adverse or other condition, or a pressure beyond a predetermined threshold, can in some embodiments prompt the control system to terminate fluid transfer, for example.

Figure 28:
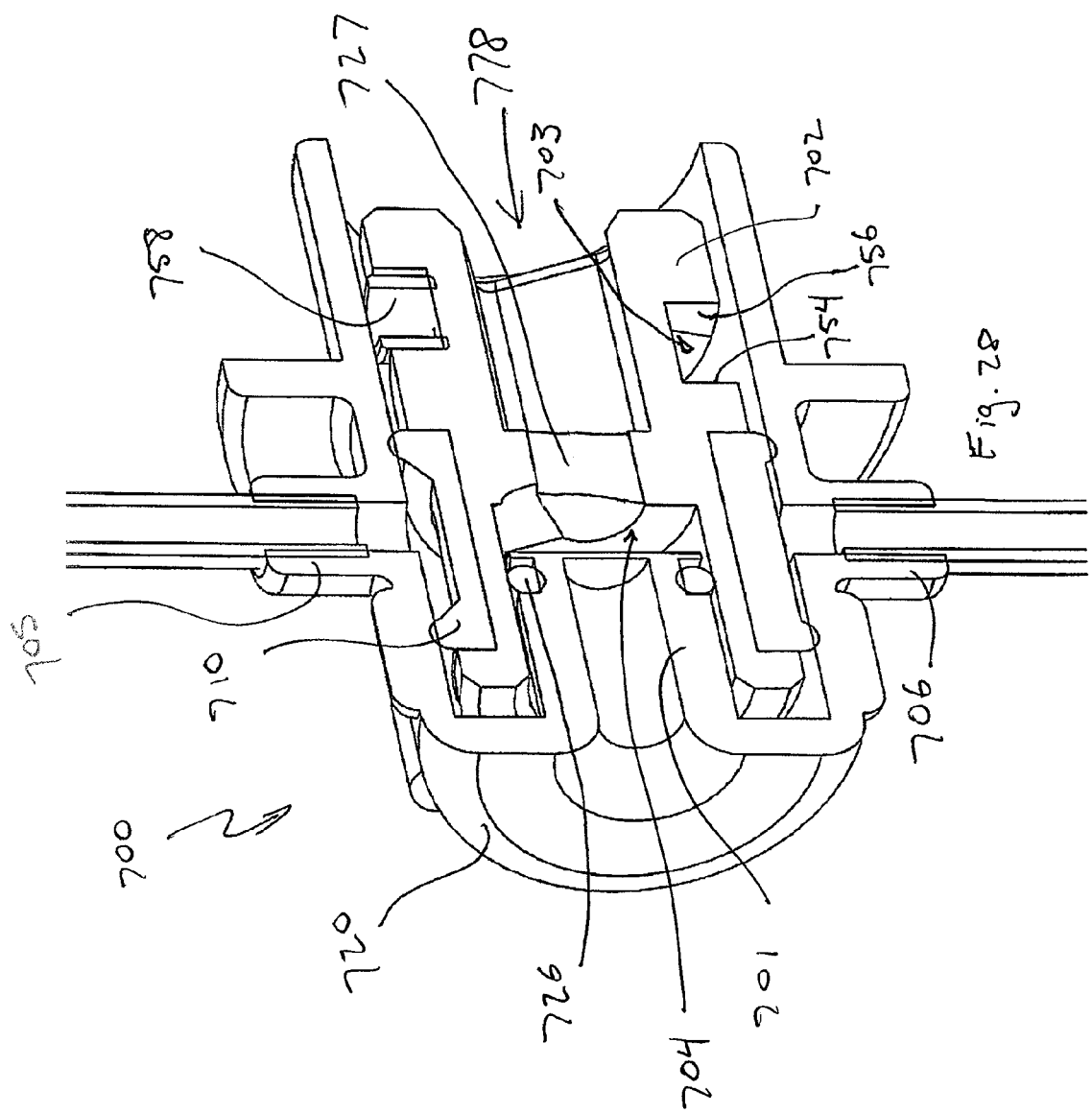
FIG. 28 is an isometric cross-sectional view of the pump assembly of the precision pump of FIG. 23 along line 28-28, shown in FIG. 26.

In some embodiments, the sensor 727 can be omitted or repositioned compared to the embodiment of FIG. 28. In such embodiments, the piston 702 can comprise a barrier separating the cavity 704 and the recess 778.

The precision pump 700, like the others disclosed herein, is scalable to suit the desired flow or pressure requirements. Advantageously, the precision pump 700 would meet the requirements of a standard infusing pump while significantly reducing both size and cost.

As a safety feature, the fluid pathway through the pump does not allow for a free-flow condition, except in the unlikely event of multiple seal failures. That is, the inlet and outlet ports are never in direct connection, being separated by at least two seals.

Fluid Delivery to the Body

From the pump for syringe, the fluid can be delivered to the body by a delivery device at a terminal end that can be connected to the pump or syringe either directly or by a conduit, such as a tube, for example. The delivery device can comprise a needle, cannula, microneedle, or other transcutaneous, subcutaneous, or intravenous fluid delivery devices for the delivery of fluids and/or chemicals into a person. For example, the conduct can feed to a patch, such as shown in FIG. 29.

Figure 29:
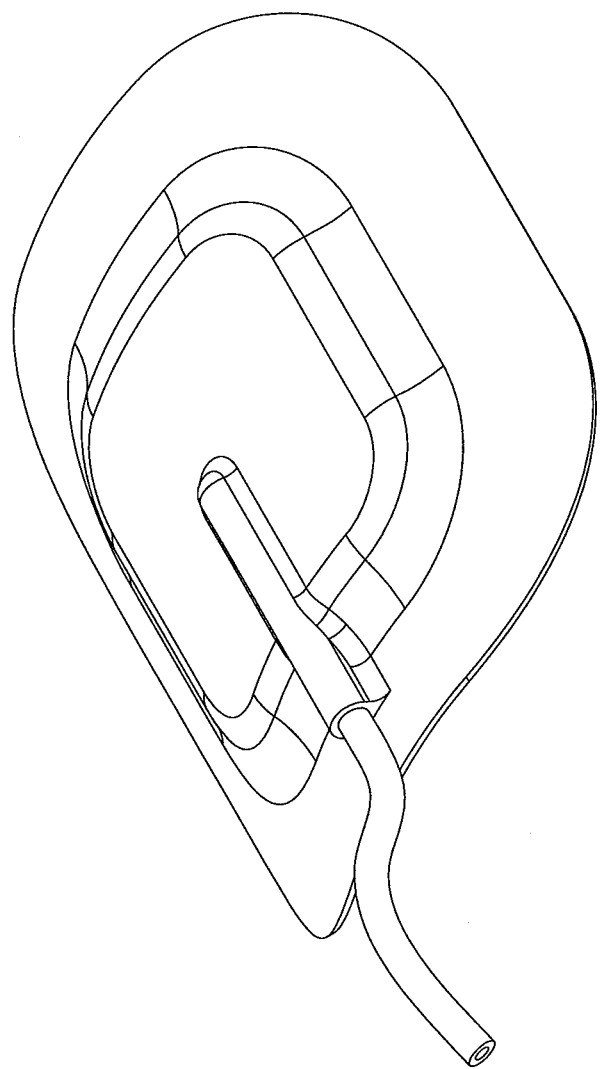
FIG. 29 is an isometric view of a skin patch which can be adapted to an embodiment of a precision pump according to an embodiment.
Figure 30:
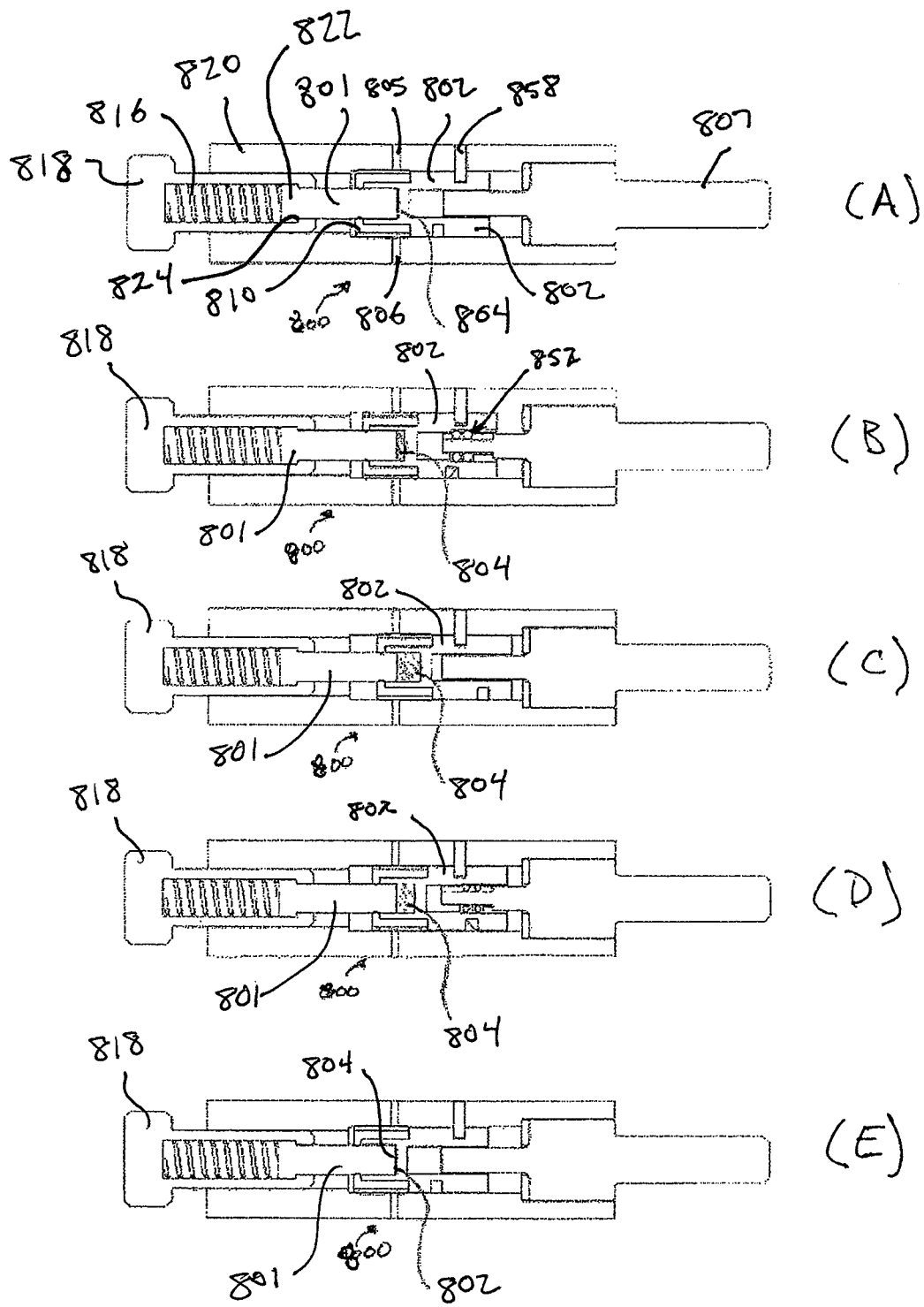
FIGS. 30A-E are cross-sectional views of an adjustable cavity precision pump according to an embodiment illustrating operation of the pump in a maximum volume configuration.
Figure 31:
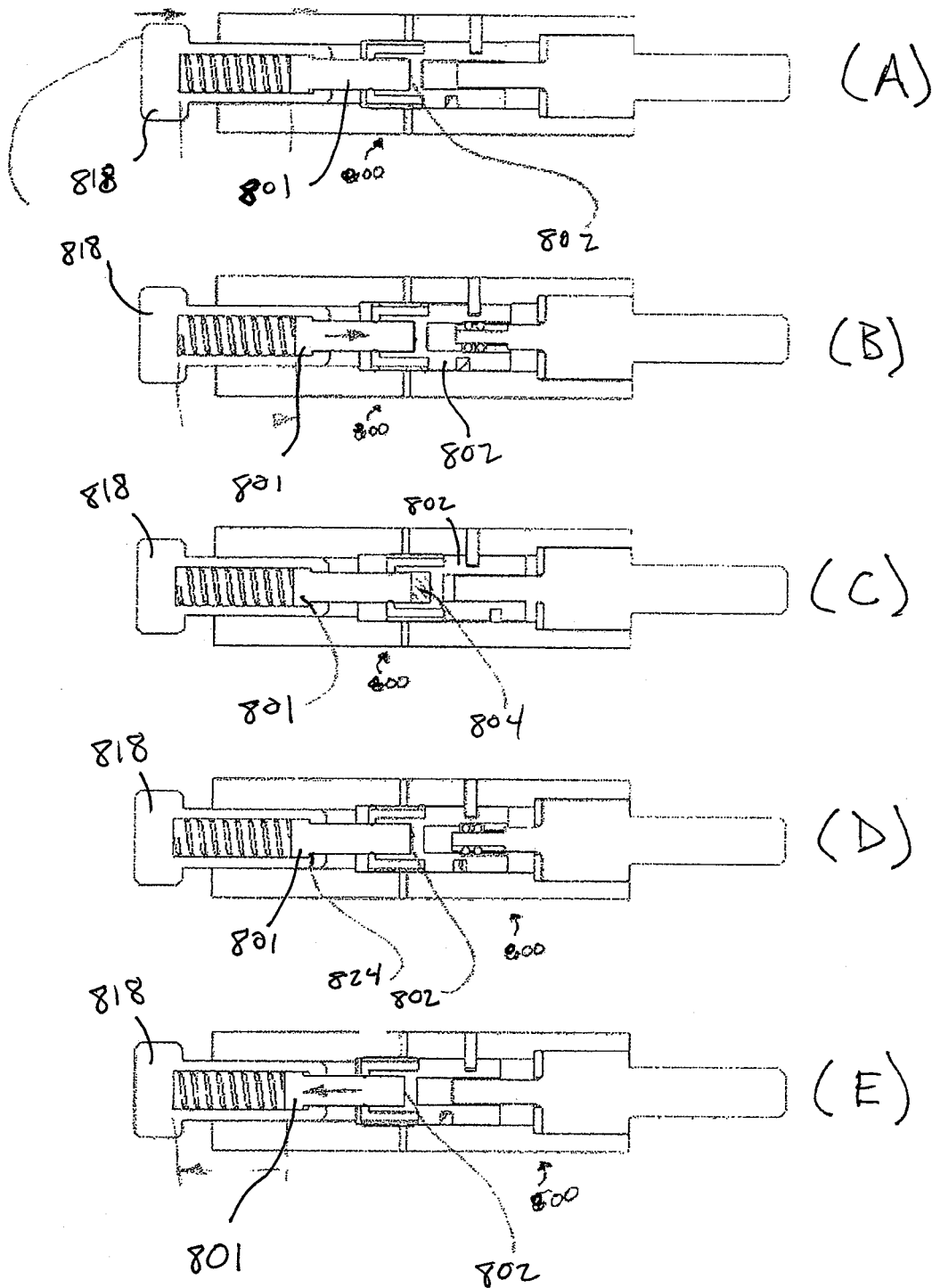
FIGS. 31A-E are cross-sectional views of the adjustable cavity precision pump of FIGS. 30A-E illustrating operation of the pump in a reduced volume configuration.

The patch of FIG. 29 comprises an adhesive for bonding to the skin. By way of example only, a fluid delivery device can deliver very small (e.g. fractions of a microliter) doses of fluid into at least a portion of a patch attached to a person's arm, leg, abdomen, back or other body part, which would allow the person's skin to absorb the fluid within the patch at a generally determined rate. The patch can comprise, for example, an absorbent material or gel that receives the fluid delivered from the pump, either directly or through a conduit, and then elutes the fluid through the skin.

Open-Loop Operation

Advantageously, some embodiments of the precision pumps disclosed herein can run open-looped with significantly predictable accuracy. Since a rigid volumetric cavity is formed within the precision pumps (within either an annular or central cavity), the transfer of a specific volume of fluid is consistent with every cycle that the precision pump undergoes. Therefore the total amount of fluid volume dispensed over a select number of cycles can be determined with a relatively large percentage of accuracy. This is in part due to the fact that the transfer of fluids is not dependent upon factors (e.g. pressure, vacuum) which are known to those skilled in the art to vary and cause inconsistencies (particularly over time) in the amount of fluid that is dispensed per cycle.

Adjustment of the Displacement Cavity

Various cavity adjustment features, such as those described below, can be incorporated into the precision pumps in some embodiments. Adjustability of the maximum volume of the displacement cavity can advantageously allow the same pump to be used to provide different flow rates without modifying the speed, or range of speeds, of the drive or input. The output characteristics can thereby be changed ratio metrically.

FIGS. 30-37 illustrate exemplifying embodiments of precision pumps that include displacement cavities having adjustable volumes. These precision pumps are similar to other illustrated precision pumps described herein in some respects, thus similar reference numerals are used in connection with these precision pumps to designate components that are similar to those of other precision pumps described herein. Thus, rather than repeat the description of similar components, it should be understood that the description of similar components herein also can also apply to the similarly numbered components of this embodiment. These precision pumps are different from the other precision pumps disclosed herein in some respects, such as those noted below.

FIGS. 30(A)-(E) and 31(A)-(E) illustrate an exemplifying embodiment of a precision pump 800 wherein a cavity adjustment feature enables the adjustment of the maximum volume of the cavity formed within the pump. The pump 800 comprises a spring loaded piston post or pin 801 that dictates the volume of the cavity formed within the precision pump 800 and can be adjusted to reduce or enlarge the cavity 804 formed at the furthest (retracted) extent of the stroke piston 802. Therefore, the volume of fluid that is transferred through the precision pump 800 with each stroke of the piston can be tuned or calibrated to the desired dispensing volume.

The precision pump 800 comprises a spring-loaded pin or plunger 801. The pin or plunger 801 is movably positioned within the housing 820. A cap, plug, or stop 818 is adjustably attached to the housing 820. A spring 816 is positioned within the housing 820 to engage the stop 818 and the pin 801 on a side of the pin that is opposite the piston 802, and urges the pin 801 toward the piston 802.

The pin 801 and stop 818 can be configured such that when the pin 801 is fully advanced the pin is seated against stop 818. For example, the pin 801 can comprise a shoulder 822 and the stop 818 can comprise a rim 824, the shoulder and the rim being sized and shaped to engage one another when the pin 801 is advanced by the spring 816 toward the rim 824. Thus, movement the stop 818 into or out of the housing 820 adjusts the maximum distance the pin 801 can advance in the direction of the piston 802.

FIGS. 30(A) and 31(A) show the piston 802 in a position of farthest advancement toward the stop 818. FIGS. 30(B) and 31(B) show the piston 802 in a position retracted from the position of farthest advancement toward the stop 818. FIGS. 30(C) and 31(C) show the piston 802 in a position farthest retraction from the pin 801. FIGS. 30(D) and 31(D) show the piston 802 in a position advanced toward the pin 801 from the position of farthest retraction from the pin 801. FIGS. 30(E) and 31(E) illustrate the piston 802 returned to the position of farthest advancement toward the stop 818.

FIGS. 30(A)-(E) illustrate operation of the pump 800 when the stop 818 is adjusted for transfer of a maximum volume of fluid. As illustrated in FIG. 30(E), when the piston 802 is at its most advanced position in the direction of the stop 818, the cavity 804 has closed and has no volume, or approximately no volume.

FIGS. 31(A)-(E) illustrate operation of the pump 800 when the stop 818 is adjusted for transfer of less than a maximum volume of fluid. As illustrated in FIG. 31(D), before the piston 802 is at its most advanced position in the direction of the stop 818, the cavity 804 has closed and has no volume, or approximately no volume. If the spring-loaded pin or plunger 801 engages the piston 802 and the piston 802 is advanced toward the stop 818, the plunger 801 will move with the piston 802 against the force of the spring 816 to retract into a recess in the stop, as illustrated in FIG. 31(E), for example.

The stop 818 can comprise threads that cooperate with threads of the housing 820 for adjustment of the stop 818 relative to the housing 820. Other types of connections between the stop 818 and the housing 820 can be used in some embodiments.

The stop 818 can be adjusted during manufacturing for precision of fluid transferred with each revolution then fixed or be adjustable by a user to vary the rate of flow of the pump. In some embodiments, a fluid flow meter can be connected to an outlet of the pump and the stop 818 can be adjusted until the desired flow rate is attached. In some embodiments, the maximum volume of the cavity can be adjusted during operation of the pump. In some embodiments, the pump can comprise indicators corresponding to specific fluid flow rates to facilitate adjustment after manufacturing.

Figure 32:
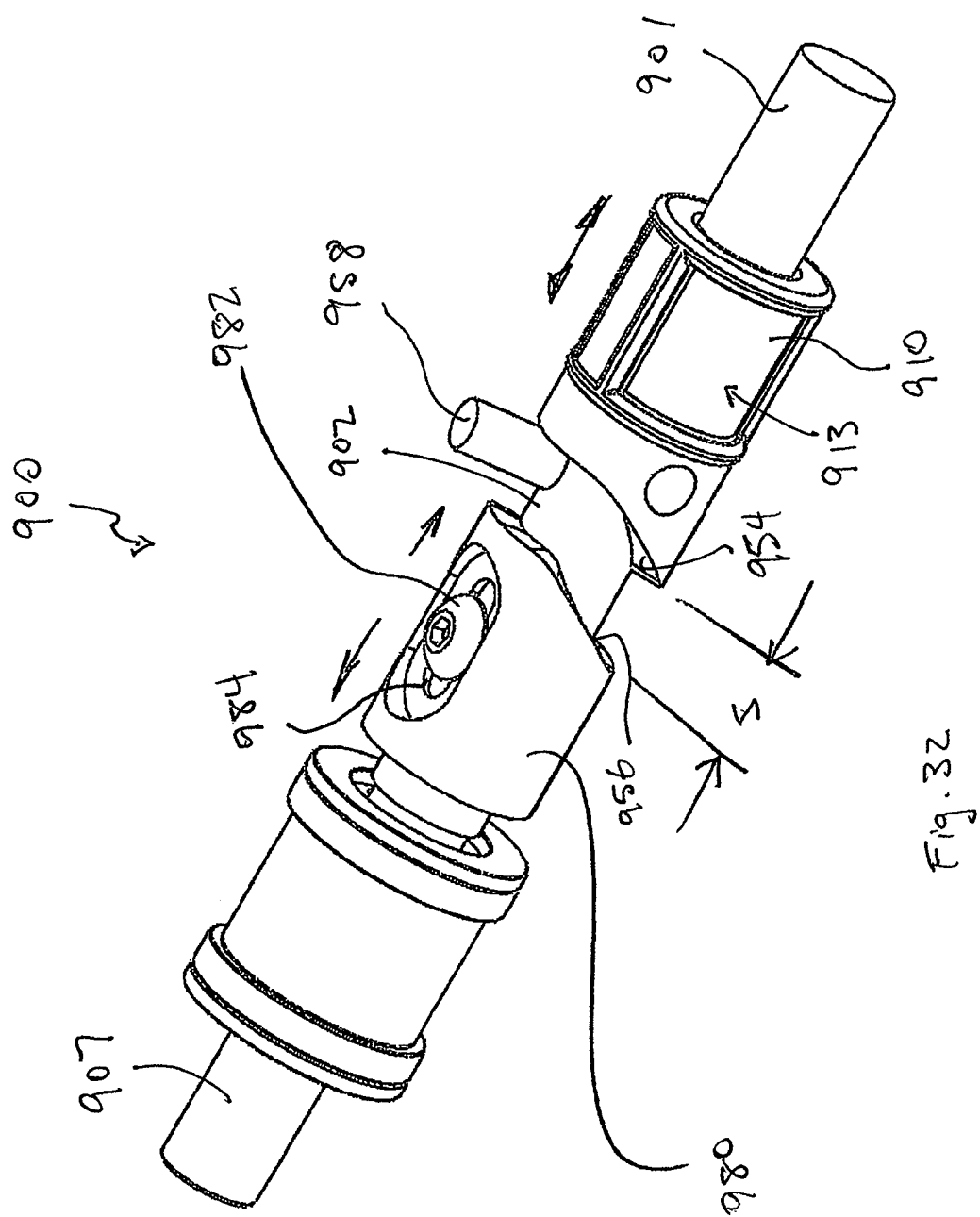
FIG. 32 is an isometric view of a portion of a precision pump comprising a cam that can be adjusted to vary the volume of fluid transferred within a cavity, according to an embodiment.
Figure 33A:
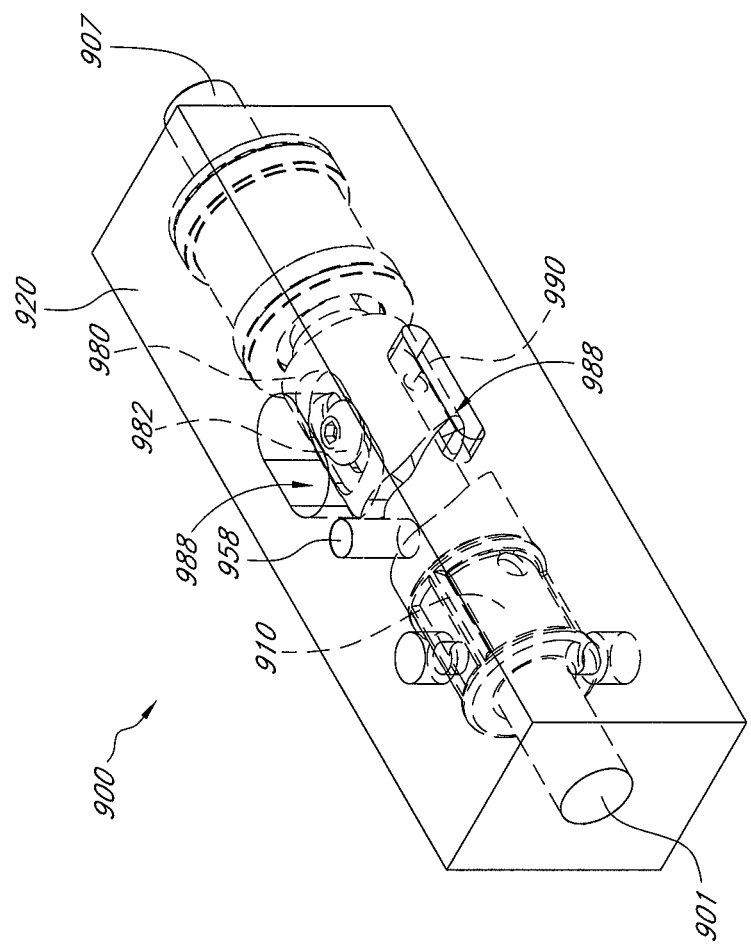
FIG. 33A is an isometric view of the precision pump of FIG. 32.
Figure 33B:
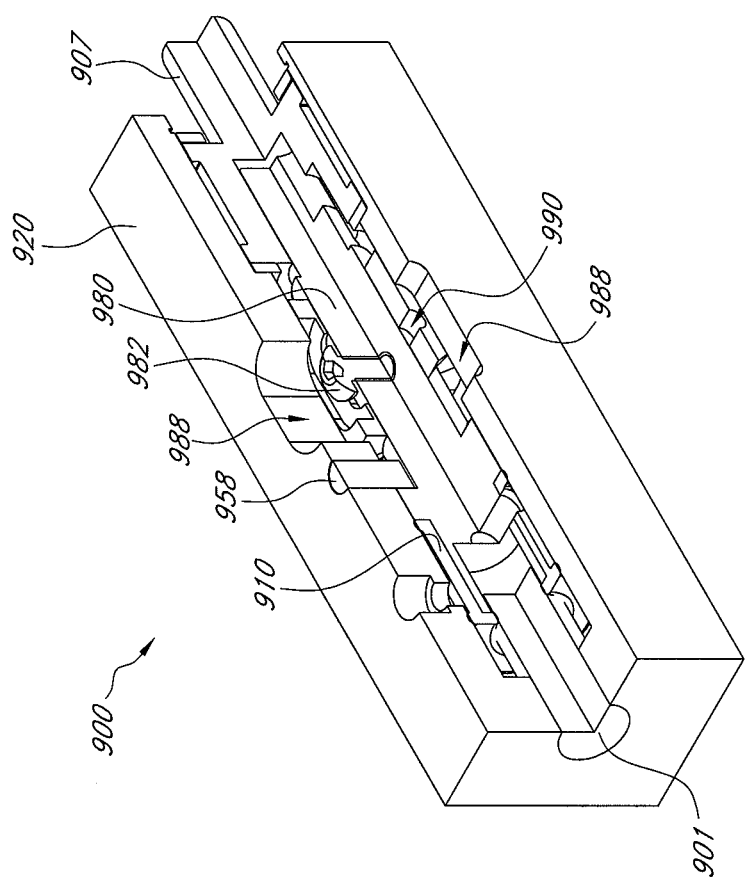
FIG. 33B is a partial cross-sectional isometric view of the precision pump of FIG. 32.
Figure 34:
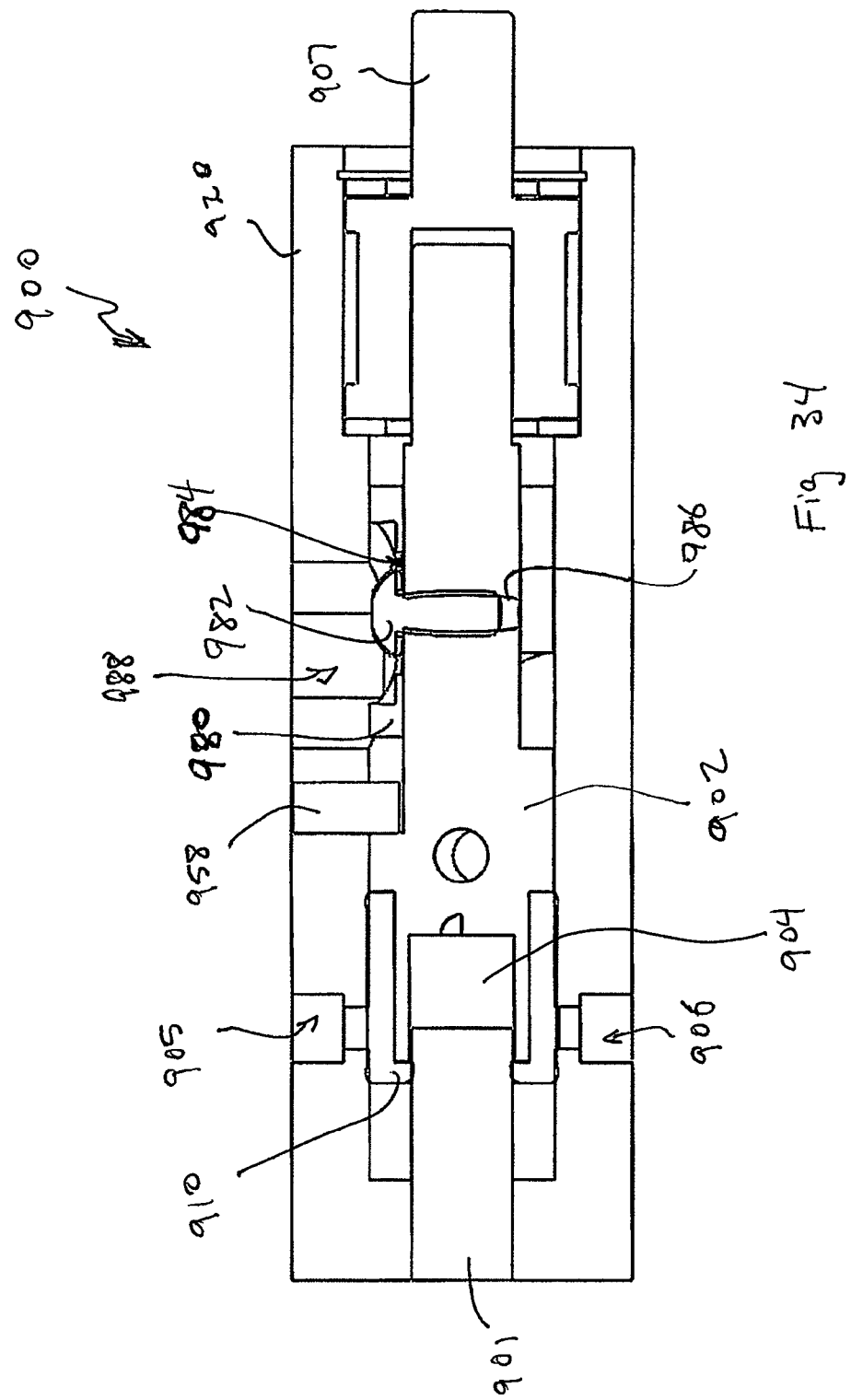
FIG. 34 is a full cross-sectional view of the precision pump of FIGS. 32 and 33.

FIG. 32-34 illustrates an exemplifying embodiment of a precision pump 900 with adjustable displacement cavity volume. In general, adjustment of the cavity volume is accomplished by causing the leading and opposing faces of the piston to be separated (or approximated) and locked into a position that results in the adjustment of the total piston stroke per revolution, which in turn governs the displacement.

Unlike the precision pump 200, described above in connection with FIGS. 12 and 13, which has a single component the piston 202 and barrel cam 203, the precision pump 900 has a piston 902 with a multi-component barrel cam system 903. The barrel cam system 903 illustrated in FIGS. 32-34 comprises an adjustable cam 980, which is slidably attached to the piston 902 to allow adjustment of the distance "S" between the guide surfaces 954, 956.

In the embodiment illustrated in FIGS. 32-34, the cam or guide surface 954, which moves the piston in a direction that expels the fluid, is integral to the piston 902. The opposing cam or guide surface 956, which retracts the piston and causes fluid to be drawn into the pump, is integral to the adjustable cam 980, which is slotted and pinned to the piston 902 to assure correct radial alignment. The adjustable cam 980 can be generally configured as a sleeve or collar, as illustrated in FIGS. 32-34, in some embodiments.

The adjustable cam 980 can be attached to the piston 902 by a set screw 982, as illustrated, or by other locking devices. The adjustable cam 980 can comprise a slot 984 extending generally along the rotational axis of the piston 902. The slot 984 and set screw 982 can be sized and spaced such that the set screw extends through the slot into an aperture 986 in the piston 902. The screw 982 can be tightened against the adjustable cam 980 to fix the adjustable cam against longitudinal movement along the piston 902.

As illustrated in FIG. 33, the housing 920 can comprise one or more access slots to facilitate moving and locking the adjustable cam 980. The access slot(s) 988, can provide access to the set screw 982 (if present) and to an aperture 990 in the adjustable cam 980. Tool(s) can be advanced through the slot(s) 988 to engage the set screw 982 (if present) and the aperture 990 to manipulate them relative to one another and, thereby, adjust the spacing distance "S" between the guide surfaces. Generally, the distance between the portions of the guide surfaces that are engaged by the pin 966, as measured along the rotational axis of the piston 902, are generally reduced as the distance "S" between the guide surfaces increases. In some embodiments, such as the one illustrated in FIGS. 32-34, the tools can be removable from the slot(s) 988 during operation to allow rotation of the adjustable cam 980 within the housing 920. The housing 920 can include indicators to assist precise and accurate selection of the distance "S". For example, the indicators can provide tactile or visional feed back to the operator.

The distance "S" can be adjusted by loosening the locking device, such as the set screw 982, if in a tightened condition. Thereafter, tools extending through the slot(s) 988 are used to adjust the spacing between the cam or guide surfaces 954, 956. Once the desired distance "S" has been obtained, the locking feature is secured. For example, the set screw is tightened.

Figure 36A:
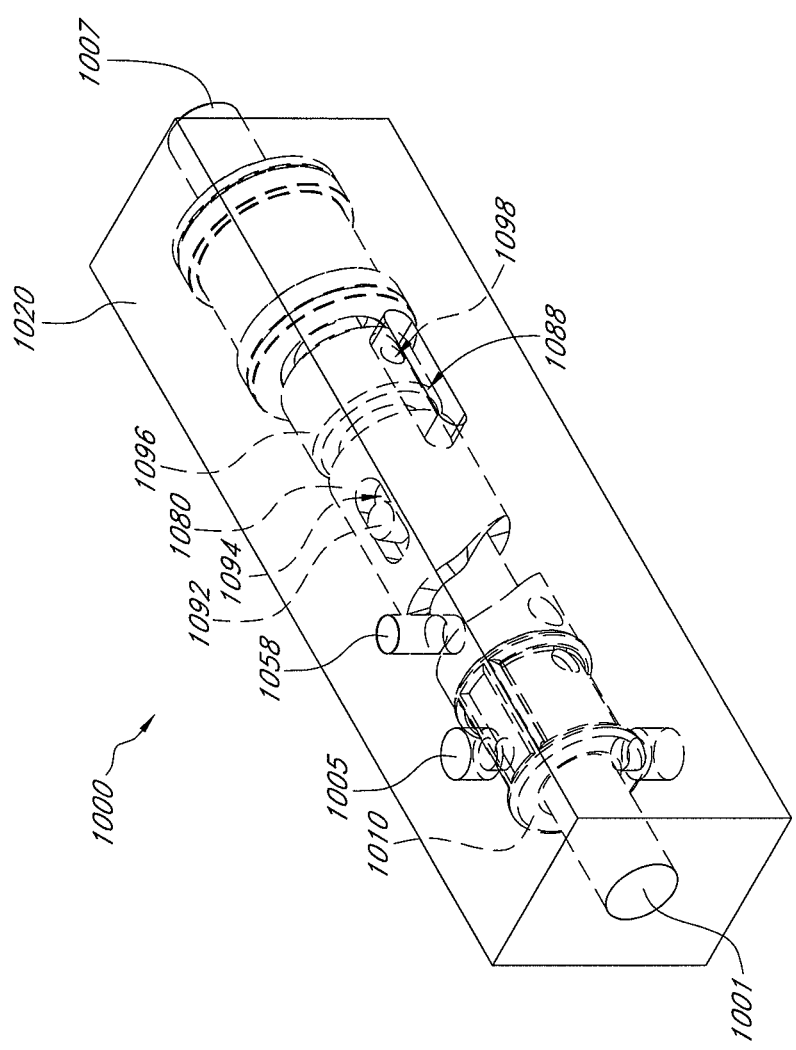
FIG. 36A is as isometric view of the precision pump of FIG. 35.
Figure 36B:
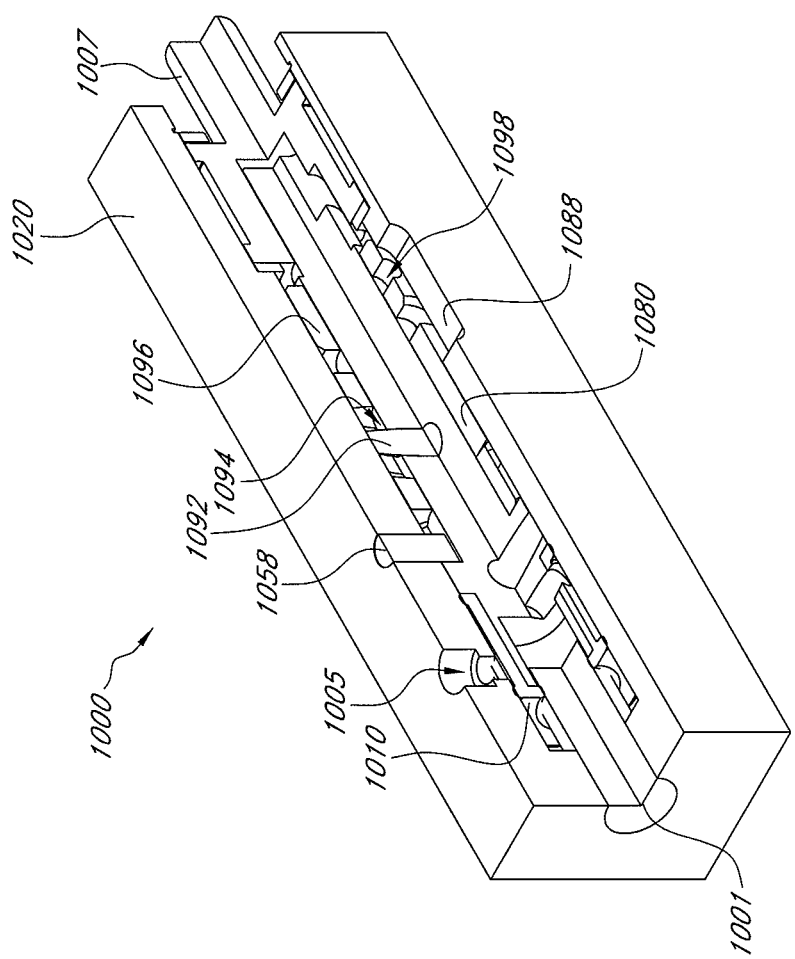
FIG. 36B is a partial cross-sectional isometric view of the precision pump of FIG. 35.

FIGS. 35-37 illustrate another exemplifying embodiment of a precision pump 1000 with a displacement cavity having an adjustable volume. The precision pump 1000 is similar to the precision pump 900, except the adjustable cam 1080 having cam or guide surface 1056 is pinned to the piston 1002 to assure correct radial alignment, but is free to float axially over the piston. In the embodiment of FIGS. 35-37, the pin 1092 is fixed to the piston 1002 and extends radially outwardly from the piston into a slot 1094 in the adjustable cam 1080. Other configuration can be used in some embodiments.

For example, a pin can be fixed to the adjustable cam and extend into a slot in the piston.

A stop 1096 is located behind the adjustable cam 1080 and is adjustable axially along the axis of rotation to limit or restrict the separation (distance "S") of the guide surfaces 1054, 1056. The stop 1096 can be adjusted through access slots 1088 in the housing 1020. The stop 1096 can be threaded onto the piston 1002 or locked with a setscrew through an aperture 1098 in the stop to facilitate its axial location. The cam pin will always move the sleeve to abut the face of the collar thus restricting the cam face separation and the resulting piston stroke and displacement.

The stop 1096 can be configured as a collar, as show in FIGS. 35-37 for example, or can have other configurations in some embodiments. In some embodiments, the aperture 1098 can be replaced with a groove extending circumferentially about the stop 1096. One or more pins, each optionally carrying a bearing, can be positioned to extend into the groove. The one or more pins can be movably connected to the housing 1020 such that the pin can be adjusted along the axis of rotation such that the maximum volume of the cavity can be adjusted while the pump is operating.

Output Pressure Compensation

Figure 38:
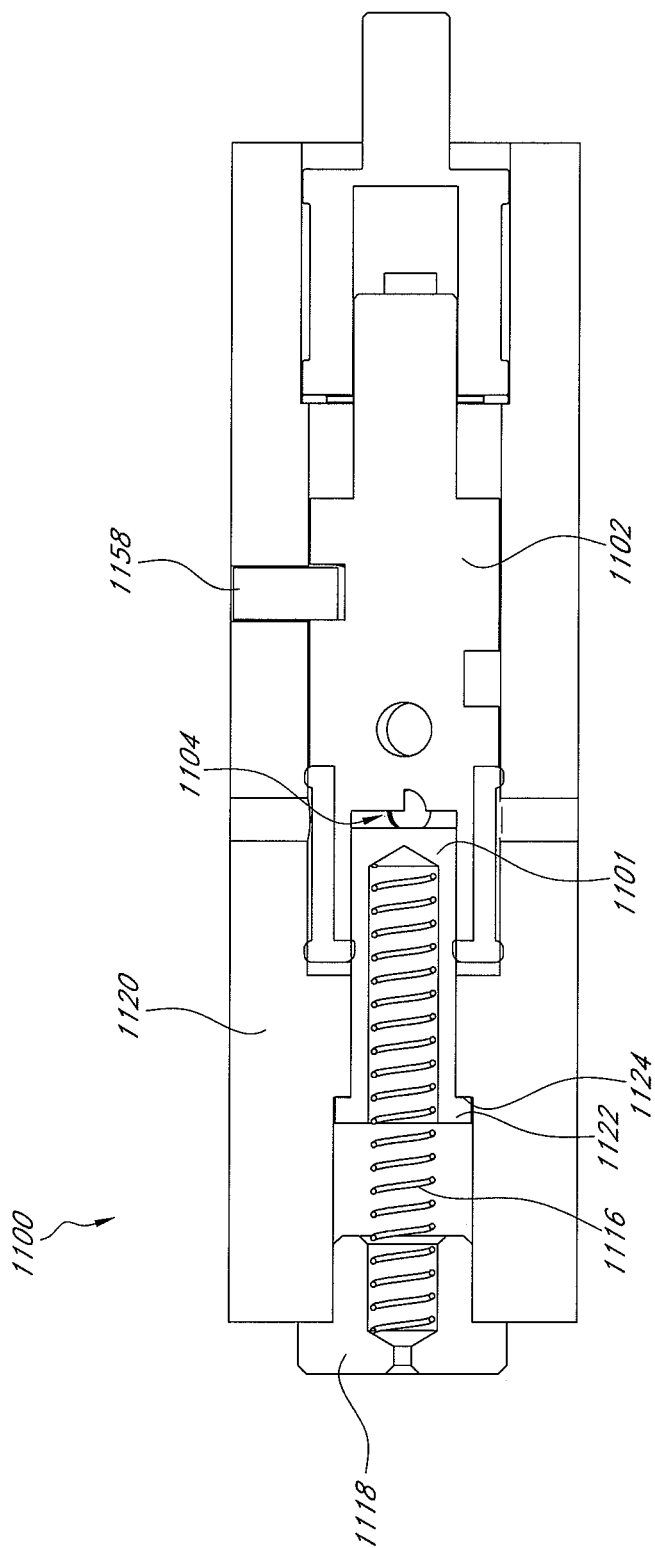
FIG. 38 is a cross-sectional view of a pressure-compensating precision pump according to an embodiment.
Figure 39:
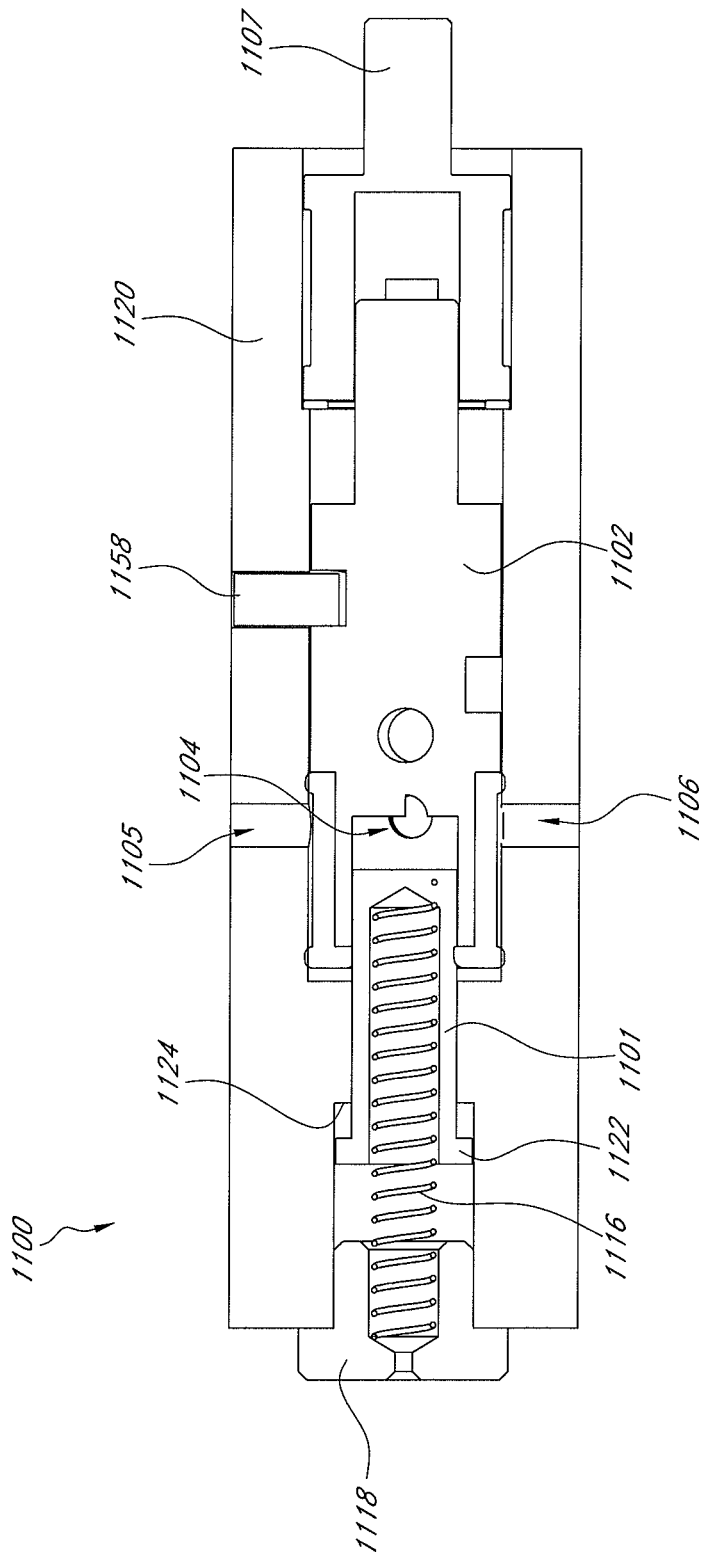
FIG. 39 is a cross-sectional view of the precision pump of FIG. 38.

FIGS. 38 and 39 illustrate an exemplifying embodiment of a precision pump 1100 capable of compensating for excess output pressure. The precision pump 1100 is similar to other illustrated precision pumps described herein in some respects, thus similar reference numerals are used in connection with the precision pump 1100 to designate components that are similar to those of other precision pumps described herein. Thus, rather than repeat the description of similar components, it should be understood that the description of similar components herein also can also apply to the similarly numbered components of this embodiment. The precision pump 1100 is different from the other precision pumps disclosed herein in some respects, such as those noted below.

Pressure at the outlet port can become elevated in some instances. Common reasons for the pressure increase include occlusion of the fluid communication line downstream of the outlet port and pressure buildup, sometimes excessive, at the delivery site.

The precision pump 1100 allows for maintaining, monitoring, and/or compensation for a maximum output pressure. The precision pump 1100 comprises a spring-loaded pin (or piston) 1101. The pin or piston 1101 is movably positioned within the housing 1120. A spring 1116 is positioned within the housing 1120 to engage the pin 1101 on a side of the pin that is opposite the piston 1102. The spring 1116 also engages a cap, plug, or stop 1118, which is attached to the housing 1120. Thus, the spring 1116 urges the pin 1101 toward the piston 1102.

The cap 1118 can be attachable to the housing 1120 in a single configuration or, in some embodiments, can facilitate adjustment of the force applied by the spring 1116 to the pin 1101. The pin 1101 and housing 1120 can be configured such that when the pin 1101 is fully advanced the pin is seated against the housing 1120. For example, the pin 1101 can comprise a shoulder 1122 and the housing cam comprise a rim 1124, the shoulder and the rim being sized and shaped to engage one another when the pin 1101 is advanced by the spring 1116 toward the piston 1102.

If the spring-loaded pin or piston 1101 experiences pressure in excess of a predetermined force correlating to the force applied by the spring 1116, the piston 1101 will move away from its fully-advanced seat in the housing and will move with the piston 1102 against the force of the spring 1116 and preclude the effluent within the chamber 1104 from being discharged to the outlet port 1106, as illustrated for example in FIG. 39.

The spring 1116 can be pre-calibrated and fixed, or adjustable through a screw type adjustment or any other adjustment suitable to vary the spring force. For example, the cap, plug, or stop 1118 can be locked in various positions of depth into the housing 1120, can be rotated to adjust compression of the spring 1116, or both. The cap 1118 can be threaded into the housing such that rotation of the cap increases or decreases compression of the spring 1116.

Axial movement of the pin or piston 1101 can be sensed by means of a switch or other sensing device as well as to realize and respond to the excessive pressure. Movement of the pin 1101 can prompt an alarm. The arm can be audible, visible, or both and can be presented at the location of the pump, transmitted to a remote location (e.g. to a caretaker), or both.

In some embodiments, the pump would automatically reset if the pressure were reduced to an acceptable level. For example, in the embodiment illustrated in FIGS. 38 and 39, once the pressure is reduced the spring 1116 again advances the pin or piston 1101 to the fully-advanced, seated configuration, thereby restoring flow to the rate of flow that existed prior to the pressure increase.

Displacement Cavity Location and Fluid Flow Path Configuration

FIGS. 40-44 illustrate exemplifying embodiments of precision pumps illustrating various locations of the displacement cavity and arrangements of the fluid flow path. These precision pumps are similar to other illustrated precision pumps described herein in some respects, thus similar reference numerals are used in connection with these precision pumps to designate components that are similar to those of other precision pumps described herein. Thus, rather than repeat the description of similar components, it should be understood that the description of similar components herein also can also apply to the similarly numbered components of this embodiment. These precision pumps are different from the other precision pumps disclosed herein in some respects, such as those noted below.

Figure 40:
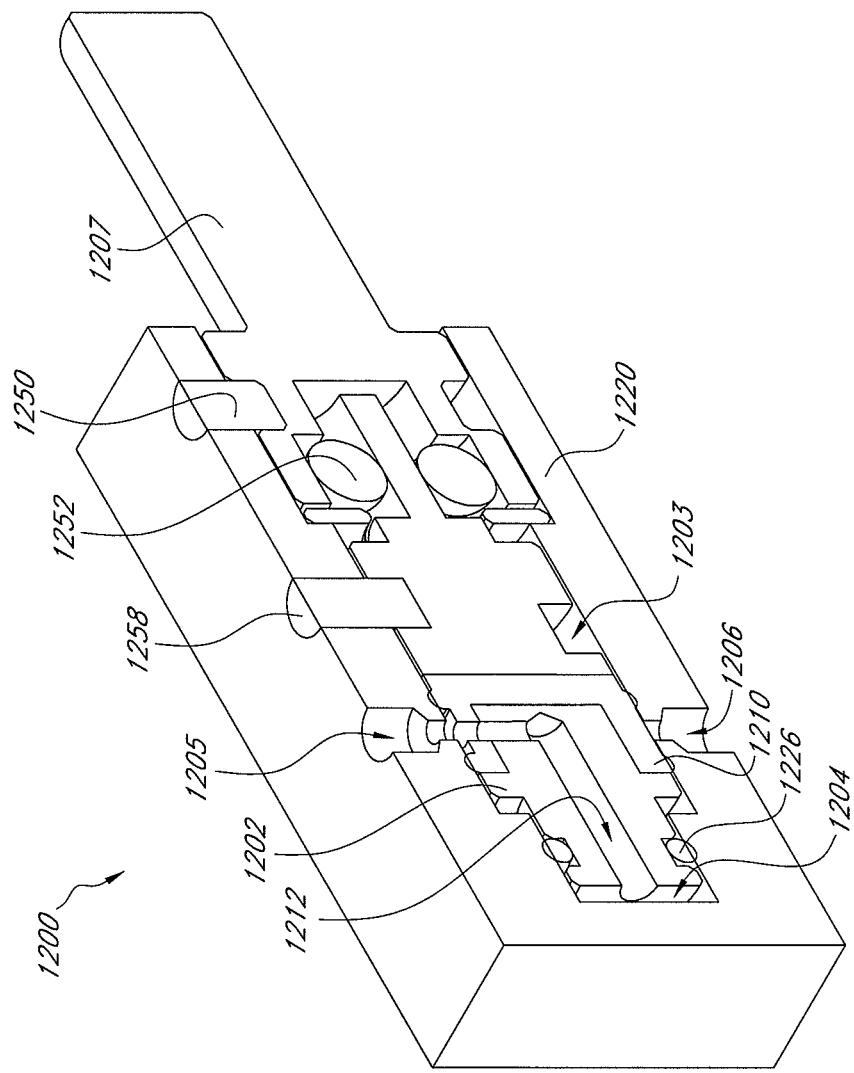
FIG. 40 is an isometric cross-sectional view of a precision pump with a pumping chamber located distally of the piston relative to a drive member, according to an embodiment.
Figure 41:
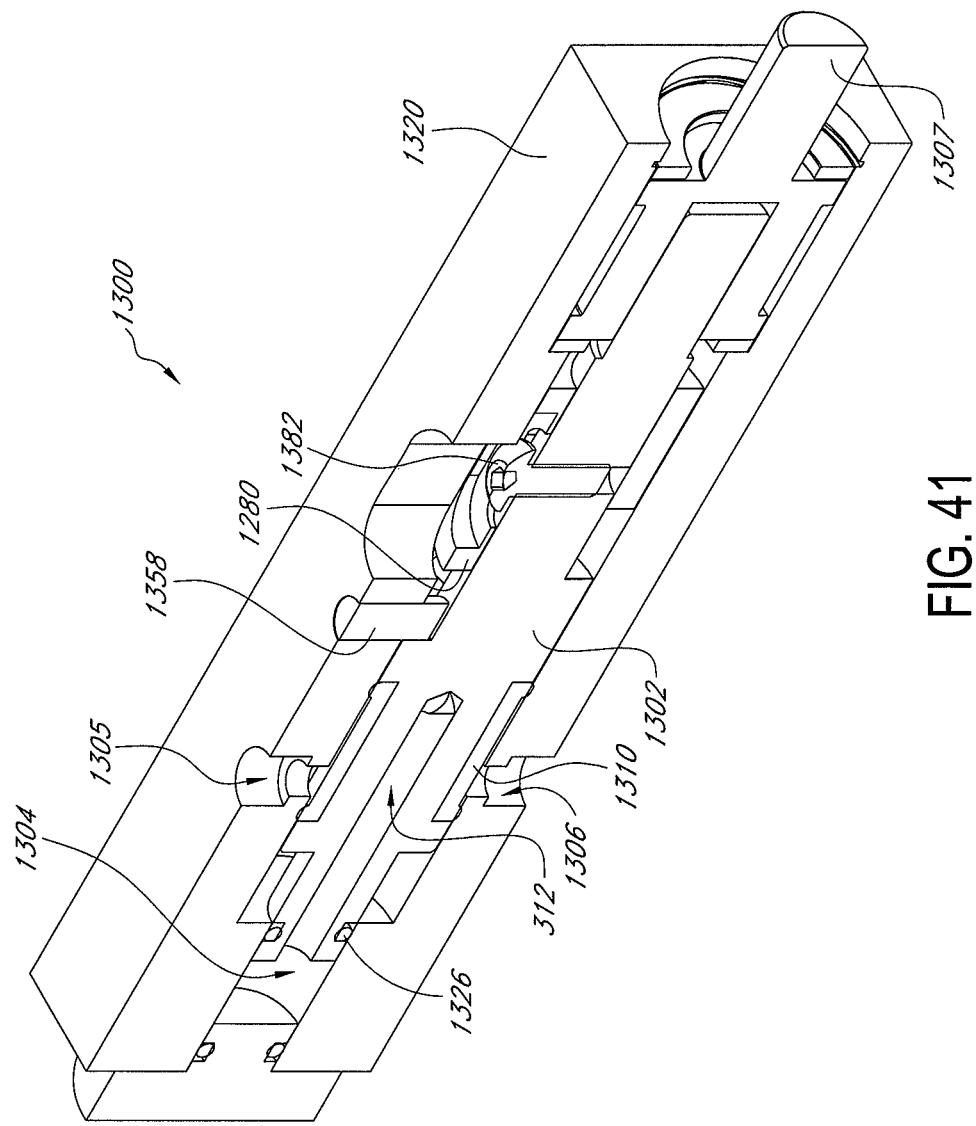
FIG. 41 is an isometric cross-sectional view of a precision pump with a pumping chamber located distally of the piston relative to a drive member and comprising a cam that can be adjusted to vary the volume of fluid transferred, according to an embodiment.

FIGS. 40 and 41 are an exemplifying embodiments of a precision pumps 1200, 1300 with a cavity 1204, 1304 located outside the piston 1202, 1302. This arrangement can advantageously allow visualization of the fluid. For example, the pump housing 1220, 1320, or a portion thereof near the cavity 204, can be made of a transparent or sufficiently translucent material to allow the fluid within the cavity to be observed by a pump user, caretaker, or technician (for example). Some embodiments wherein a circumference of the cavity about the rotational axis is formed by the housing 1220, 1320 rather than by the piston, can advantageously be easier to manufacture. For example, a pin or plunger, such as pin or plunger 201, 301, 401 can be omitted.

The fluid pathway 1212, 1312 illustrated in FIGS. 40 and 41 extends along the axis of rotation and radially for communication with the inlet and outlet ports. The portion of the fluid pathway 1212, 1312 that extends along the axis of rotation can be located on the axis, as illustrated in FIGS. 40 and 41, or offset from the axis.

The embodiments of FIGS. 40 and 41 omit a pin or piston forming a boundary of the cavity 1204, 1304. Rather the housing 1220, 1320 together with the piston 1202 define the cavity. In the embodiment of FIG. 40, the housing 1220 comprises a blind hole that cooperates with the piston 1202 to define the cavity. On the other hand, in the embodiment of FIG. 41, the housing 1320 comprises a through hole and a cap that cooperate with the piston 1302 to define the cavity.

FIGS. 40 and 41 illustrate one example of how various features disclosed herein can be combined in various arrangements. In contrast to the embodiment of FIG. 40, the embodiment of FIG. 41, as illustrated, also includes adjustability of the volume of the cavity, such as is described above in connection with FIGS. 32-34. The embodiments of FIGS. 40 and 41 can be modified to include any of the cavity volume adjustment features disclosed herein. Modification of the embodiment of FIG. 40 to include the mechanism shown in FIGS. 30 and 31 for adjusting of the volume of the cavity would require creating an opening in the housing 1220 to receive the adjustable stop and movable pin or plunger.

The embodiments of FIGS. 40 and 41 each comprise a valve seal 1210, 1310 and may, in some embodiments such as those illustrated, include a separate, independent seal 1226, 1326 (e.g. an o-ring) on the piston 1202, 1302 to seal the cavity 1204, 1304, rather than being integrated with molded with the rotating valve/transfer seal 1210, 1310. Similarly, the other precision pumps disclosed herein can comprise separate seals for the cavity and for opening and closing communication between the flow path 1212, 1312 and the inlet and outlet ports.

Figure 42:
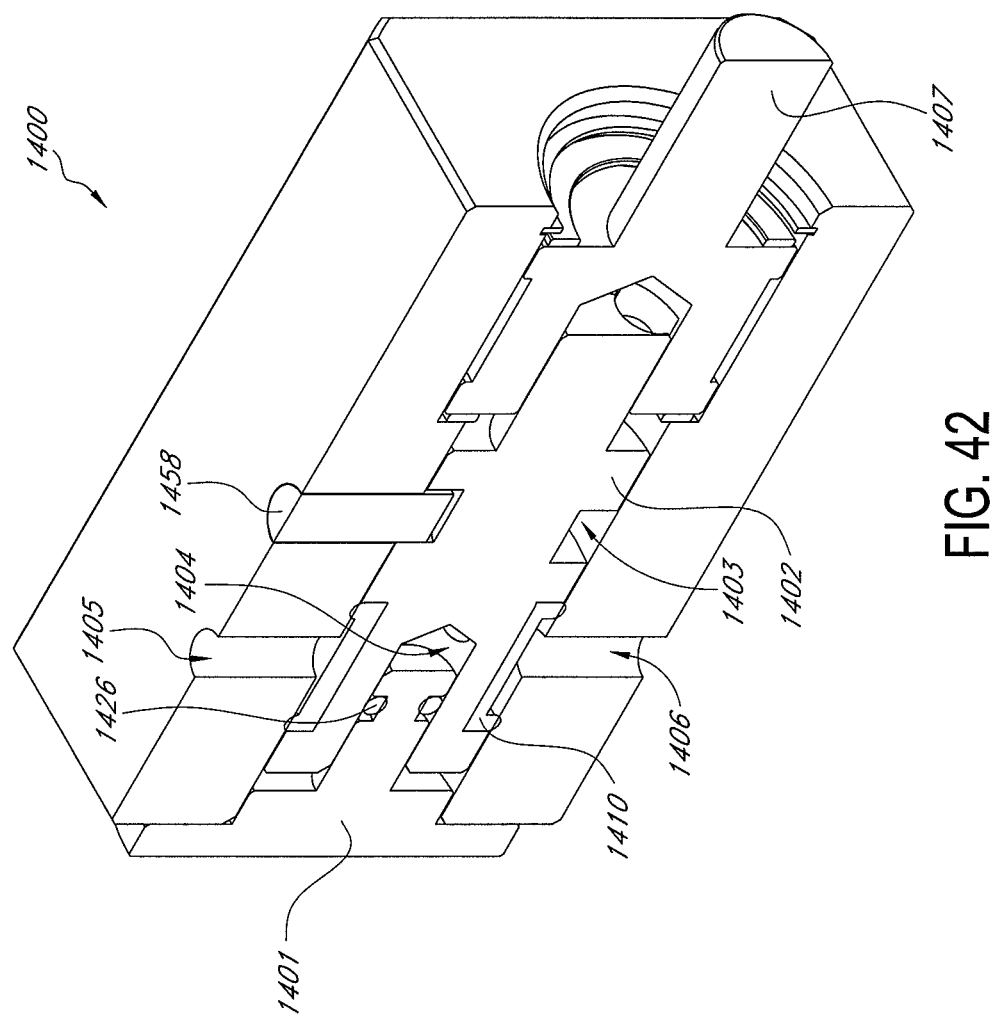
FIG. 42 is an isometric cross-sectional view of a precision pump comprising a plurality of seals, including an o-ring, according to an embodiment.

FIG. 42 is an exemplifying embodiment of a precision pump 1400 with a cavity 1404 bounded by a pin 1401 and the piston 1402 and comprises separate seals for sealing the cavity 1404 and controlling communication through the inlet and outlet ports.

Figure 43:
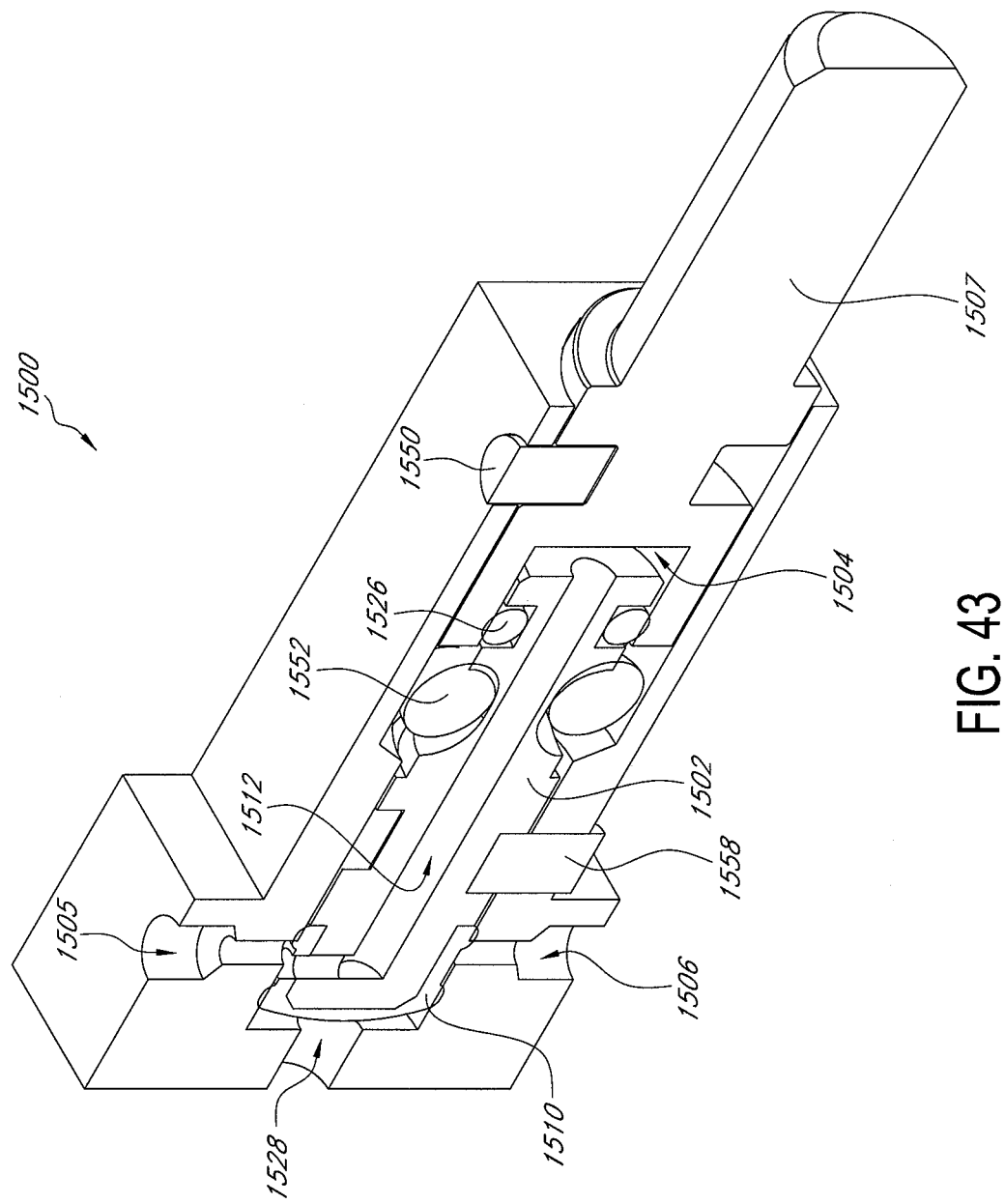
FIG. 43 is an isometric cross-sectional view of a precision pump comprising a pumping chamber positioned between a drive member and a piston, according to an embodiment.

FIG. 43 is an exemplifying embodiment of a precision pump 1500 with a cavity located between the piston 1502 and the drive or input shaft 1507. This arrangement can be used advantageously to conserve space in smaller applications.

Figure 44:
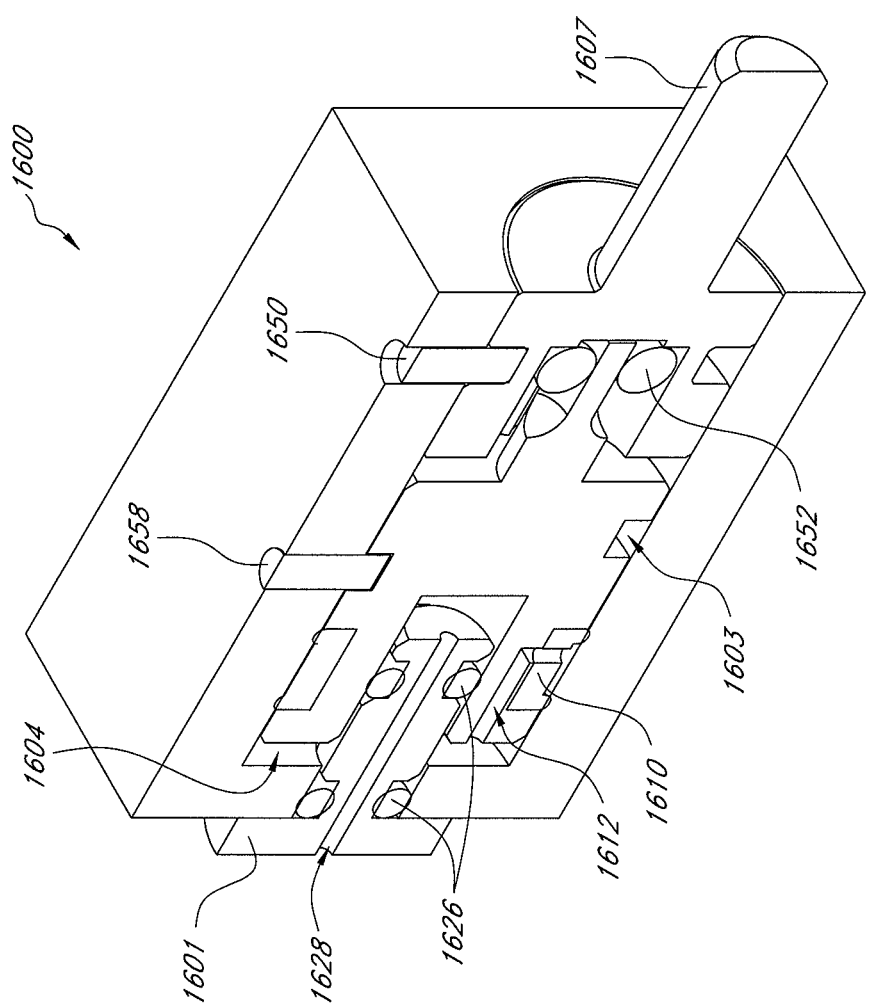
FIG. 44 is an isometric cross-sectional view of a precision pump comprising an annular pumping chamber according to an embodiment.

FIG. 44 is an exemplifying embodiment of a precision pump 1600 with a cavity 1604 configured and positioned around the pin 1601 as an annular chamber. This annular configuration can, in some embodiments, advantageously increase the precision of the volume dispensed per stroke compared to a centrally located cavity. The pin 1601 can also comprise a vent port 1628.

Miscellaneous Features

Figure 45:
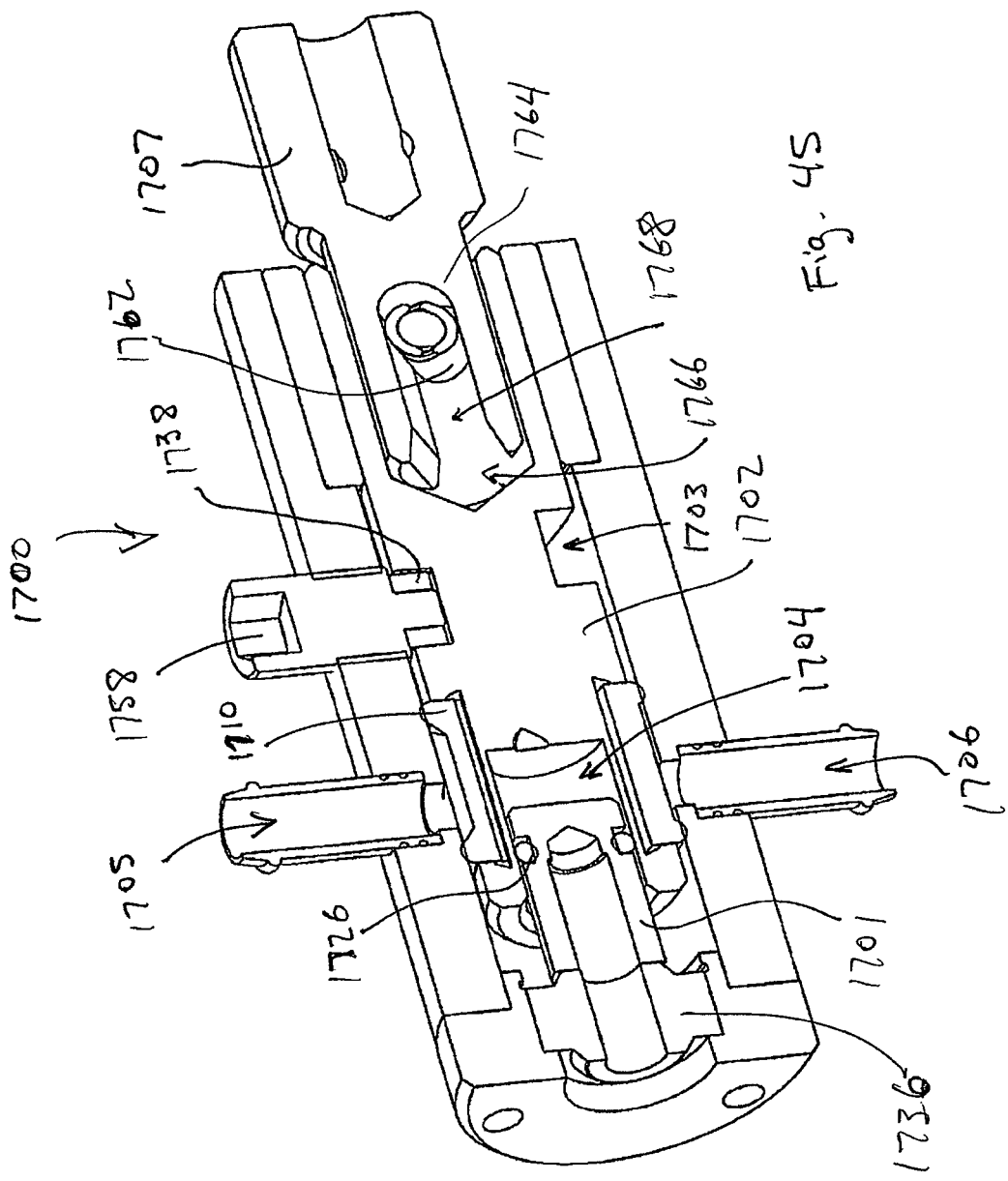
FIG. 45 is an isometric cross-sectional view of a precision pump comprising a self-aligning plunger post according to an embodiment.
Figure 46:
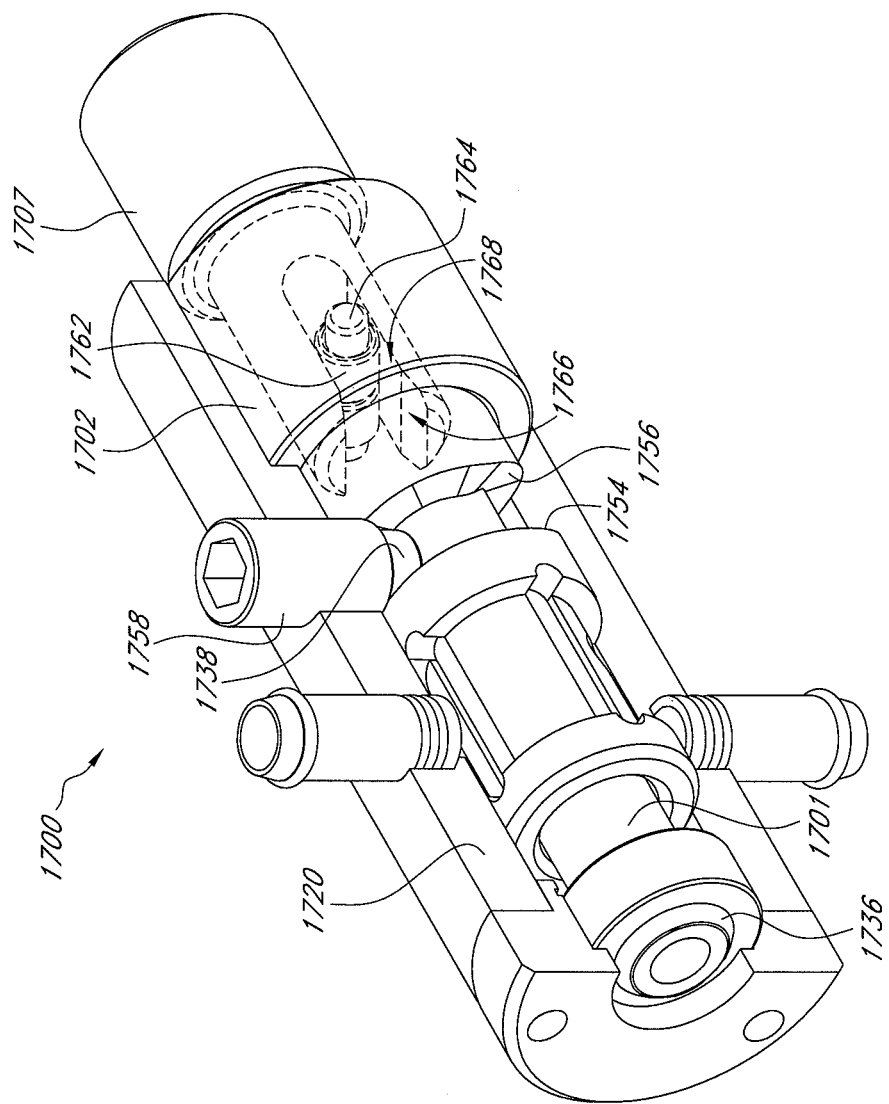
FIG. 46 is an isometric view of a portion of the precision pump of FIG. 45.

FIGS. 45 and 46 illustrate an exemplifying embodiment of a precision pump 1700 illustrating a self-aligning spherical bearing on which the piston is allowed to move freely within the pump chamber. The precision pump 1700 is similar to other illustrated precision pumps described herein in some respects, thus similar reference numerals are used in connection with this precision pump to designate components that are similar to those of other precision pumps described herein. Thus, rather than repeat the description of similar components, it should be understood that the description of similar components herein also can also apply to the similarly numbered components of this embodiment. The precision pump 1700 is different from the other precision pumps disclosed herein in some respects, such as those noted below.

The precision pump 1700 comprises a self-aligning spherical bearing 1736, which can advantageously reduce side loads on both the piston seal 1726 and the rotation valve seal 1710 for improved seal and friction performance in some embodiments. The bearing 1736 can allow the pin or piston 1701 to revolve with the piston chamber (or piston) 1702 thus reducing friction between seal 1726 and either or both of the pin 1701 and the piston 1702.

In some embodiments, as illustrated in FIGS. 45 and 46 for example, the inlet port 1705 and the outlet port 1706 of can be sized for transfer of highly-viscous substances, such as adipose. In some embodiments, the inner diameter of the inlet and outlet ports is equal to or greater than exactly or about ⅛ inch and equal to or less than exactly or about ½ inch. The inner diameter of the inlet and outlet ports can be equal to exactly or about ¼ inch in some embodiments.

The precision pump 1700 of FIGS. 45 and 46 comprises a coupling that allows radial and axial translation of the piston 1702 relative to the drive or input shaft 1707. The piston 1702 comprises rollers 1762 mounted on an axle 1764 in a recess 1766 of the piston 1702. The drive or input shaft 1707 comprises a fork that is sized and shaped to straddle the rollers 1762 upon reception in the recess 1766. The fork comprises a slot 1768 of sufficient size to receive the rollers 1762. Other types of couplings between the input shaft and piston that allow axial and radial translation of the piston relative to the input shaft while transferring rotational movement, such as the ball and groove arrangement described above, can be used in other embodiments.

The precision pump 1700 comprises a roller bearing 1738 at the end of the pin 1758 that extends into engagement with the barrel cam 1703. The roller bearing 1738 can advantageously reduce friction and cam wear when utilized. All of the above features can be applied to all of the previously disclosed configurations as may be dictated by specific applications.

In some embodiments, the precision pumps disclosed herein are advantageously reversible, self-priming, positive displacement, disposable, and capable of pumping viscous fluids and, as such, are suitable for applications such as fat transfer including collection, delivery and re-depositing through appropriately sized lumen. Although the foregoing description refers to fluids in connection with the structure and operation of various devices as an exemplifying substance that can be transferred, it shall be understood that any substance that can be drawn into and dispensed from the pump can be used.

Reversible operation of the pumps disclosed herein can provide one or more advantages, such as those that follow. For example, reversible operation can permit a reservoir (or other container) to be filled then dispensed without disconnecting the reservoir from an outlet then connecting the reservoir to an inlet. Reversible operation can allow blood to be drawn into a fluid delivery line to confirm proper insertion of a delivery device. Reversible operation can allow KVO (keep vein open) operation by periodically moving fluid (or other substance) back and forth. Reverse operation can be manually actuated or directed by a control system, e.g. a computer or other control device, governing operation of a driver.

In some embodiments, the precision pumps disclosed herein can be manufactured at a relatively low cost compared to existing technologies and therefore suitable for disposable applications in some instances. Some embodiments of the disclosed pumps are well suited for commercial applications requiring disposable precision such as lab-on-a-chip diagnostic or assay type applications were highly accurate micro dose flows are required.

Embodiments of the precision pumps that are configured to mix fluids together are ideal for precision ratio-metric applications at the point of use, such as adhesive applications (e.g. multi-part epoxies).

The precision pumps disclosed herein can be scalable (both large and small) to meet the needs of their intended use and can be adapted to various driving mechanisms (e.g. cams, motors) and systems in some embodiments.

Scope of the Invention and Nature of the Foregoing Description

Although described with respect to specific examples of the different embodiments, any feature of the fluid dispensing systems (e.g. precision syringes and precision pumps) are disclosed herein by way of example only may be applied to any of the other embodiments without departing from the scope of the present invention. While this invention has been described in terms of a best mode for achieving this invention's objectives, it will be appreciated by those skilled in the art that variations may be accomplished in view of these teachings without deviating from the spirit or scope of the invention.

What is claimed is:

1. A pump for delivery of precise volumes of a substance, comprising:
    a housing comprising a bore therein;
    a piston positioned within the bore and configured for simultaneous rotational and axial reciprocal movement within the bore along an axis,
    wherein said reciprocal movement acts to increase and decrease the volume of a chamber;
    a fluid path through the piston that is movable between a first position where the fluid path is in fluid communication with an inlet and a second position where the fluid path is in fluid communication with an outlet, and
    wherein the rotational movement moves the fluid path between the first position and the second position.

2. The pump of claim 1, wherein the chamber has an annular shape.

3. The pump of claim 1, wherein the piston comprises at least one cam surface configured to cooperate with a cam follower attached to the housing.

4. The pump of claim 3, wherein a maximum volume of the chamber is adjusted by moving the cam surface along the axis.

5. The pump of claim 1, wherein the pump is configured to compensate for pressure within the chamber above a predetermined maximum pressure.

6. The pump of claim 1, further comprising at least a second inlet.

7. The pump of claim 1, further comprising a spherical bearing at least partially supporting the piston.

8. The pump of claim 1, further comprising a reservoir in fluid communication with the inlet.

9. The pump of claim 1, wherein the input comprises a rotational single input, wherein rotation results in reciprocation of the piston and increases or decreases the volume of the chamber.

10. The device of claim 1, wherein the piston and a shaft within the piston are reciprocated relative to the housing.

11. The device of claim 1, wherein the chamber is configured to be adjusted to reach a maximum volumetric capacity.

12. The device of claim 1, wherein a rate of the decrease in the volume of the chamber can be reduced in response to a pressure at the outlet greater than a predetermined maximum pressure.

* * * * *